US010808242B2

(12) United States Patent
Kariko et al.

(10) Patent No.: US 10,808,242 B2
(45) Date of Patent: Oct. 20, 2020

(54) METHOD FOR REDUCING IMMUNOGENICITY OF RNA

(71) Applicant: BioNTech RNA Pharmaceuticals GmbH, Mainz (DE)

(72) Inventors: Katalin Kariko, Rydal, PA (US); Ugur Sahin, Mainz (DE)

(73) Assignee: BIONTECH RNA PHARMACEUTICALS GMBH, Mainz (DE)

( * ) Notice: Subject to any disclaimer, the term of this patent is extended or adjusted under 35 U.S.C. 154(b) by 226 days.

(21) Appl. No.: 15/755,309

(22) PCT Filed: Aug. 24, 2016

(86) PCT No.: PCT/EP2016/070012
§ 371 (c)(1),
(2) Date: Feb. 26, 2018

(87) PCT Pub. No.: WO2017/036889
PCT Pub. Date: Mar. 9, 2017

(65) Prior Publication Data
US 2019/0153428 A1 May 23, 2019

Related U.S. Application Data

(63) Continuation-in-part of application No. PCT/EP2015/069760, filed on Aug. 28, 2015.

(51) Int. Cl.
| | | |
|---|---|---|
| A61K 48/00 | (2006.01) | |
| C12N 15/10 | (2006.01) | |
| C12N 15/67 | (2006.01) | |
| C12P 19/34 | (2006.01) | |
| C12N 15/88 | (2006.01) | |
| C07K 14/505 | (2006.01) | |

(52) U.S. Cl.
CPC .......... *C12N 15/102* (2013.01); *C07K 14/505* (2013.01); *C12N 15/10* (2013.01); *C12N 15/67* (2013.01); *C12N 15/88* (2013.01); *C12P 19/34* (2013.01)

(58) Field of Classification Search
CPC ...... A61K 48/00; C12N 15/102; C12N 15/10; C12N 15/67; C12P 19/34; C07K 14/505
See application file for complete search history.

(56) References Cited

U.S. PATENT DOCUMENTS

2005/0032730 A1  2/2005  Von Der Mulbe et al.
2012/0142756 A1† 6/2012  Guild

FOREIGN PATENT DOCUMENTS

| JP | 2008504827 A | 2/2008 | |
| WO | 2006002538 A1 | 1/2006 | |
| WO | 2009/095226 A2 | 8/2009 | |
| WO | 2009095226 A2 † | 8/2009 | |
| WO | 2011/012316 A2 | 2/2011 | |
| WO | 2011012316 A2 † | 2/2011 | |
| WO | 2013/151664 A1 | 10/2013 | |
| WO | 2013151666 A2 | 10/2013 | |
| WO | 2014/160243 A1 | 10/2014 | |
| WO | 2014160243 A1 † | 10/2014 | |
| WO | WO-2015062738 A1 * | 5/2015 | .............. C12P 19/34 |

OTHER PUBLICATIONS

Anderson, B.R. et al. "Incorporation of pseudouridine into mRNA enhances translation by diminishing PKR activation", Nucleic Acids Research, vol. 38. No. 17, May 10, 2010, pp. 5884-5892.
Atkinson, S.D. et al. "Development of Allele-Specific Therapeutic siRNA for Keratin 5 Mutations in Epidermolysis Bullosa Simplex", Journal of Investigative Dermatology, vol. 131, 2011, pp. 2079-2086.
Bentz, E. et al: "A polymorphism of the CYP17 gene related to sex steroid metabolism is associated with female-to-male but not male-to-female transsexualism", Fertility and Sterility, vol. 90, No. 1, Jul. 1, 2008, pp. 56-59.
Kariko, K. et al:, "Incorporation of pseudouridine into mRNA yields superior nonimmunogenic vector with increased translational capacity and biological stability", Molecular Therapy, vol. 16,. No. 11, Nov. 2008, pp. 1833-1840.
Kim, C.H. et al. "Codon optimization for high-level expression of human erythropoietin (EPO) in mammalian cells", Gene, vol. 199, 1997, pp. 293-301.
Thess, A. et al, "Sequence-engineered mRNA Without Chemical Nucleoside Modifications Enables an Effective Protein Therapy in Large Animals", Molecular Therapy, vol. 23, No. 9, Sep. 2015, pp. 1456-1464.
Alter, G. et al., "Single-Stranded RNA Derived from HIV-1 Serves as a Potent Activator of NK Cells", The Journal of Immunology, 2007, vol. 178, pp. 7658-7666.
Heil, F. et al., "Species-Specific Recognition of Single-Stranded RNA via Toll-like Receptor 7 and 8", Science, Mar. 2004, vol. 303, pp. 1526-1529.
Meier, A. et al., "My D88-Dependent Immune Activation Mediated by Human Immunodeficiency Virus Type 1-Encoded Toll-Like Receptor Ligands",Journal of Virology, Aug. 2007, vol. 81, No. 15, pp. 8180-8191.

(Continued)

*Primary Examiner* — Valarie E Bertoglio
(74) *Attorney, Agent, or Firm* — Olson & Cepuritis, Ltd.

(57) ABSTRACT

The present invention relates to RNA therapy and, in particular, decreasing immunogenicity of RNA. Specifically, the present invention provides methods for decreasing immunogenicity of RNA, said methods comprising modifying the nucleotide sequence of the RNA by reducing the uridine (U) content, wherein said reduction of the U content comprises an elimination of U nucleosides from the nucleotide sequence of the RNA and/or a substitution of U nucleosides by nucleosides other than U in the nucleotide sequence of the RNA. Using RNA having decreased immunogenicity allows administration of RNA as a drug to a subject, e.g. in order to obtain expression of a pharmaceutically active peptide or protein, without eliciting an immune response which would interfere with therapeutic effectiveness of the RNA or induce adverse effects in the subject.

7 Claims, 7 Drawing Sheets
Specification includes a Sequence Listing.

(56) References Cited

OTHER PUBLICATIONS

Pritlove, D. et al., "Polyadenylation of Influenza Virus mRNA Transcribed in Vitro from Model Virion RNA Templates: Requirement for 5' Conserved Sequences", Journal of Virology, Feb. 1998, vol. 72, No. 2, pp. 1280-1286.
Alter et al., "Single-stranded RNA derived from HIV-1 serves as a potent activator of NK cells," J. Immunol., 178:7658-7666, 2007.†
Meier et al., "MyD88-dependent immune activation mediated by human immunodeficiency virus type 1-encoded toll-like receptor ligands," J. Virol., 81:8180-8191, 2007.†
Heil et al., "Species-specific recognition of single-stranded RNA via toll-like receptor 7 and 8," Science 303:1526-1529, 2004.†
Diebold et al., "Nucleic acid agonists for toll-like receptor 7 are defined by the presence of uridine ribonucleotides," Eur. J. Immunol., 36:3256-3267, 2006.†
Anderson et al., "Incorporation of pseudouridine into mRNA enhances translating by diminishing PKR activation," Nucl. Acids Res., 38(17):5884-5892, 2010.†
Kariko et al., "Incorporation of pseudouridine into mRNA yields superior nonimmunogenic vector with increased translational capacity and biological stability," Molecular Therapy, 16(11):1833-1840, 2008.†

\* cited by examiner
† cited by third party

| Names of the murine EPO mRNA | Number of nucleotides | | | | Nucleotide composition (%) | | | | CDS |
|---|---|---|---|---|---|---|---|---|---|
| | A | G | U | C | A | G | U | C | GC |
| mEPO, wt EPO, orig. mEPO | 138 | 146 | 125 | 170 | 24% | 25% | 22% | 29% | 55% | 579 nt |
| omEPO, GC-rich | 121 | 174 | 92 | 192 | 21% | 30% | 16% | 33% | 63% | |
| somEPO | 132 | 160 | 127 | 160 | 23% | 28% | 22% | 28% | 55% | |
| A-rich, U-poor | 195 | 141 | 80 | 163 | 34% | 24% | 14% | 28% | 53% | |
| GC-maximized | 91 | 185 | 84 | 219 | 16% | 32% | 15% | 38% | 70% | |

B

| Names of the canine mRNA | | | | | | | | | | |
|---|---|---|---|---|---|---|---|---|---|---|
| cEPO, wtEPO, orig. cEPO | 125 | 176 | 124 | 196 | 20% | 28% | 20% | 32% | 60% | 621 nt |
| A-rich, U-poor | 202 | 158 | 83 | 178 | 33% | 25% | 13% | 29% | 53% | 621 nt |

Levels of EPO & IFN alpha in plasma of mice at 6/24 h following injection of 10 µg LNP-formulated murine EPO mRNA

METHOD FOR REDUCING IMMUNOGENICITY OF RNA

CROSS-REFERENCE TO RELATED APPLICATIONS

This application is a U.S. National Stage of PCT/EP2016/070012, filed on Aug. 24, 2016, which is a continuation-in-part of International Application No. PCT/EP2015/069760, filed on Aug. 28, 2015, each of which is incorporated herein by reference.

SEQUENCE LISTING INCORPORATION

Biological sequence information for this application is included in an ASCII text file, having the file name "ZSP-136-SEQ-V2.txt", created on Jul. 24, 2018, and having a file size of 14,819 bytes, which is incorporated herein by reference.

TECHNICAL FIELD OF THE INVENTION

The present invention relates to RNA therapy and, in particular, decreasing immunogenicity of RNA. Specifically, the present invention provides methods for decreasing immunogenicity of RNA, said methods comprising modifying the nucleotide sequence of the RNA by reducing the uridine (U) content, wherein said reduction of the U content comprises an elimination of U nucleosides from the nucleotide sequence of the RNA and/or a substitution of U nucleosides by nucleosides other than U in the nucleotide sequence of the RNA. Using RNA having decreased immunogenicity allows administration of RNA as a drug to a subject, e.g. in order to obtain expression of a pharmaceutically active peptide or protein, without eliciting an immune response which would interfere with therapeutic effectiveness of the RNA or induce adverse effects in the subject.

BACKGROUND OF THE INVENTION

In vitro-transcribed mRNA (IVT mRNA) is emerging as a new drug class that has the potential to play an important role in gene therapy. While first described as a therapeutic in 1992, the immunogenicity of IVT mRNA prevented its development for protein replacement therapies. However, this problem was solved by introducing modified nucleosides into mRNA (see Karikó, K., Buckstein, M., Ni, H., and Weissman, D. (2005) Suppression of RNA recognition by Toll-like receptors: the impact of nucleoside modification and the evolutionary origin of RNA. Immunity 23, 165-175). In this study, all uridines were exchanged for pseudouridines, the most common naturally occurring modified nucleoside. Pseudouridine-modified mRNA was found to be highly translatable and non-immunogenic (see Karikó, K., Muramatsu, H., Welsh, F. A., Ludwig, J., Kato, H., Akira, S., and Weissman, D. (2008) Incorporation of pseudouridine into mRNA yields superior nonimmunogenic vector with increased translational capacity and biological stability. Molecular therapy 16, 1833-1840). An alternative solution was to replace 25% of the uridine residues with 2-thiouridine (s2U), resulting in an mRNA with some residual immunogenicity (see Kormann, M. S., Hasenpusch, G., Aneja, M. K., Nica, G., Flemmer, A. W., Herber-Jonat, S., Huppmann, M., Mays, L. E., Illenyi, M., Schams, A., Griese, M., Bittmann, I., Handgretinger, R., Hartl, D., Rosenecker, J., and Rudolph, C. (2011) Expression of therapeutic proteins after delivery of chemically modified mRNA in mice. Nature biotechnology 29, 154-157).

Recently, an alternative method for generating therapeutically applicable IVT mRNA was reported that does not require the use of modified nucleosides (see Thess, A., Grund, S., Mui, B. L., Hope, M. J., Baumhof, P., Fotin-Mleczek, M., and Schlake, T. (2015) Sequence-engineered mRNA without chemical nucleoside modifications enables an effective protein therapy in large animals. Molecular Therapy 23, 1457-1465). In this study, the sequence composition of the mRNA was altered by selecting codons with the highest GC-rich content for each amino acid. The study indicates that such GC-maximized mRNAs may have the potential to reduce immune activation and thereby to improve translation and half-life of the mRNA.

However, lack of immunogenicity of the codon-optimized GC-maximized sequences has not been demonstrated unequivocally in this study since the test IVT mRNA was formulated with TransIT®, a commercially available complexing agent. It is known that TransIT®-formulated RNA primarily induces IFN-α (see Karikó, K., Muramatsu, H., Ludwig, J., and Weissman, D. (2011) Generating the optimal mRNA for therapy: HPLC purification eliminates immune activation and improves translation of nucleoside-modified, protein-encoding mRNA. Nucleic acids research 39, e142), but IFN-α induction was not measured in any of the experiments performed by Thess and colleagues. As a consequence, the level of reduction of immune activation by means of using GC-maximized mRNAs and the therapeutical benefit of this method remains unclear.

Thus, it is an object of the present invention to provide an alternative and even superior method for generating therapeutically applicable and non-immunogenic RNA, in particular IVT mRNA which likewise does not require the use of modified nucleosides.

It is demonstrated herein that mRNA constructs with low uridine and increased adenosine content have low immunogenicity. Both immunogenicity and translatability of these A-rich (U-poor) mRNAs were compared to the corresponding wild-type (wt) mRNAs in vitro in human dendritic cells (DCs) and in vivo in BALB/c mice.

SUMMARY OF THE INVENTION

The present invention is directed to methods of altering RNA such as eukaryotic, preferably mammalian, mRNA which result in a reduced immunogenicity of the RNA and enables its use in RNA therapy, e.g. to provide a peptide or protein of interest. The invention also pertains to compositions comprising such RNA. The invention also relates to RNA therapy, e.g., the use of RNA described herein as a drug in order to obtain the expression of a therapeutically relevant peptide or protein within a cell. The subject compositions and methods are useful in treating a myriad of disorders involving errors in expression of proteins.

In one aspect the invention relates to a method of decreasing immunogenicity of RNA, said method comprising modifying the nucleotide sequence of the RNA by reducing the uridine (U) content, wherein said reduction of the U content comprises an elimination of U nucleosides from the nucleotide sequence of the RNA and/or a substitution of U nucleosides by nucleosides other than U in the nucleotide sequence of the RNA.

In one embodiment, the method comprises the steps of:
(i) providing the nucleotide sequence of a first RNA,
(ii) designing the nucleotide sequence of a second RNA, said nucleotide sequence of the second RNA comprising a reduced U content compared to the nucleotide sequence of the first RNA, and, optionally, (iii) providing the second RNA.

In a further aspect the invention relates to a method of providing a nucleic acid molecule for RNA transcription comprising the steps of:

(i) providing a first DNA sequence encoding the nucleotide sequence of a first RNA, (ii) designing a second DNA sequence encoding the nucleotide sequence of a second RNA, said nucleotide sequence of the second RNA comprising a reduced U content compared to the nucleotide sequence of the first RNA, wherein said reduction of the U content comprises an elimination of U nucleosides from the nucleotide sequence of the RNA and/or a substitution of U nucleosides by nucleosides other than U in the nucleotide sequence of the RNA, and (iii) providing a nucleic acid molecule comprising the second DNA sequence.

In one embodiment of the methods of the invention, the RNA encodes at least one peptide or protein. In one embodiment, the peptide or protein is pharmaceutically active or antigenic. In one embodiment, the amino acid sequence of the peptide or protein encoded by the RNA modified by reducing the U content is identical to the amino acid sequence of the peptide or protein encoded by the non-modified RNA.

In one embodiment of the methods of the invention, said reduced U content renders the RNA modified by reducing the U content less immunogenic compared to the non-modified RNA.

In one embodiment of the methods of the invention, the U content in the RNA modified by reducing the U content is reduced by at least 10%, preferably at least 20%, more preferably at least 30% compared to the non-modified RNA.

In one embodiment of the methods of the invention, the U content is reduced in one or more of the 5' untranslated region, the coding region and the 3' untranslated region of the RNA. In one embodiment of the methods of the invention, the U content is reduced in the coding region of the RNA.

In one embodiment of the methods of the invention, said reduction of the U content comprises a substitution of U nucleosides by nucleosides other than U in the nucleotide sequence of the RNA.

In one embodiment of the methods of the invention, said nucleosides other than U are selected from the group consisting of adenosine (A), guanosine (G), 5-methyluridine (m5U) and cytidine (C).

In one embodiment of the methods of the invention, said reduction of the U content comprises a substitution of U nucleosides by adenosine (A) nucleosides.

In one embodiment of the methods of the invention, said reduction of the U content comprises altering codons which comprise at least one U nucleoside by other codons that encode the same amino acids but comprise fewer U nucleosides and preferably comprise no U nucleosides.

In one embodiment, the methods of the invention further comprise introducing at least one analogue of a naturally occurring nucleoside into the nucleotide sequence of the RNA. In one embodiment, introducing the analogue of a naturally occurring nucleoside into the nucleotide sequence of the RNA reduces immunogenicity of the RNA. In one embodiment, introducing at least one analogue of a naturally occurring nucleoside into the nucleotide sequence of the RNA comprises a substitution of U nucleosides by pseudouridines.

In one embodiment of the methods of the invention, the RNA is mRNA.

In a further aspect the invention relates to a method of obtaining RNA comprising the steps of (i) providing a nucleic acid molecule for RNA transcription according to the method of the invention of providing a nucleic acid molecule for RNA transcription, and (ii) transcribing RNA using the nucleic acid molecule as a template.

In a further aspect the invention relates to a modified RNA having decreased immunogenicity compared to naturally occurring RNA, said modified RNA having a nucleotide sequence comprising a reduced U content compared to said naturally occurring RNA, wherein said reduction of the U content comprises an elimination of U nucleosides from the nucleotide sequence of the RNA and/or a substitution of U nucleosides by nucleosides other than U in the nucleotide sequence of the RNA.

Embodiments of the RNA of the invention are as described above for the methods of the invention.

RNA described herein may be employed, for example, for transient expression of genes, with possible fields of application being RNA pharmaceuticals which are administered for transient expression of functional recombinant proteins such as erythropoietin, hormones, coagulation inhibitors, etc., in vivo.

In a further aspect the invention relates to a method of treating a subject using RNA comprising the steps of (i) decreasing immunogenicity of RNA according to the method of the invention of decreasing immunogenicity of RNA, and (ii) administering the RNA to the subject.

In a further aspect the invention relates to a method of treating a subject using RNA comprising the steps of (i) obtaining RNA according to the method of the invention of obtaining RNA, and (ii) administering the RNA to the subject.

In a further aspect the invention relates to a method of treating a subject comprising administering the RNA of the invention to the subject.

In one embodiment, the RNA described herein is administered repetitively to a subject. In one embodiment, the RNA described herein is administered to a subject so as to be introduced into cells of the subject for expression of the peptide or protein encoded by the RNA.

In one particularly preferred embodiment, the RNA described herein is in vitro transcribed RNA. In one embodiment, the RNA described herein is modified by pseudouridine and/or 5-methylcytidine.

In one embodiment, decreasing the U content results in a reduction of immunogenicity of the RNA compared to the situation where the U content is not reduced.

In one particularly preferred embodiment of the invention, the RNA which is modified by reducing the U content has an increased A content and preferably a reduced GC content compared to non-modified RNA.

BRIEF DESCRIPTION OF THE DRAWINGS

FIG. 1A shows the nucleotide compositions of mRNAs coding for wild type murine EPO (wt EPO), GC-rich murine EPO (also called optimized murine EPO/omEPO), A-rich murine EPO, and GC-maximized murine EPO as described in Thess, A., Grund, S., Mui, B. L., Hope, M. J., Baumhof, P., Fotin-Mleczek, M., and Schlake, T. (2015). FIG. 1B shows the nucleotide compositions of mRNAs coding for wild type canine EPO (wt EPO) and A-rich canine EPO (cEPO).

Figure 5:
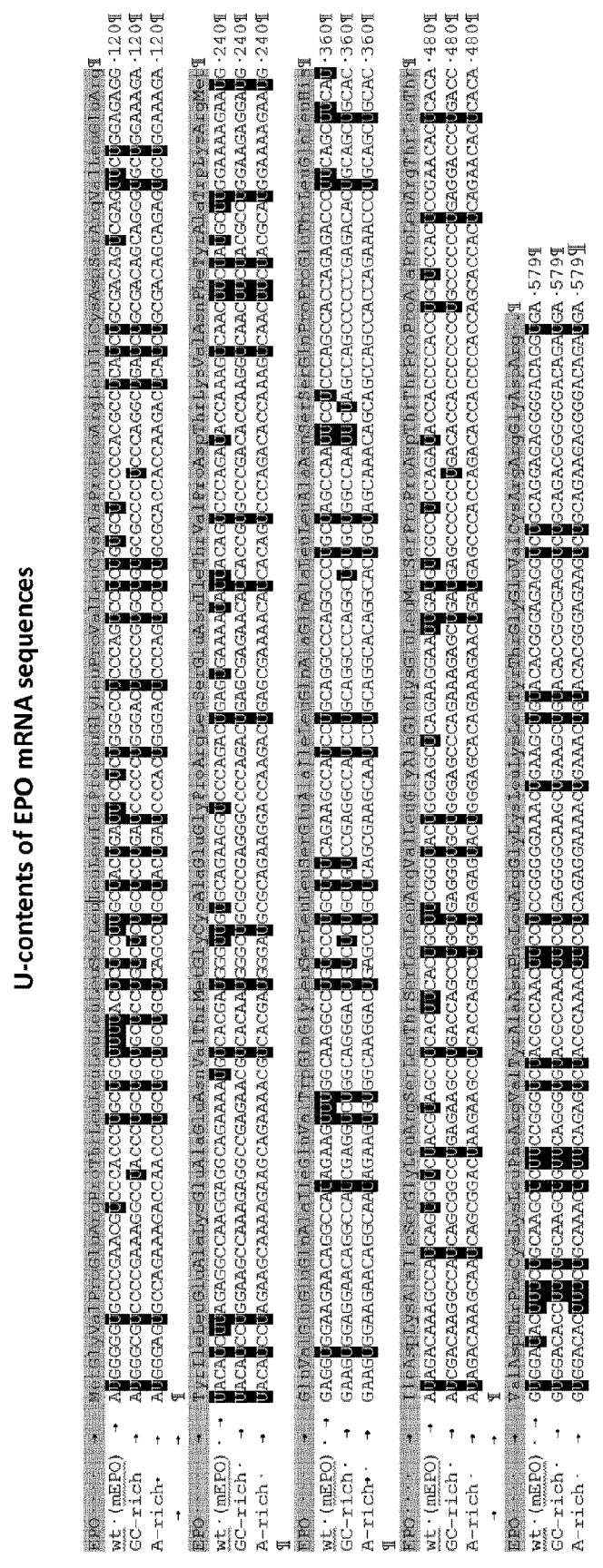

FIG. 5 shows a comparison of the uridine contents of murine EPO encoding wild type mRNA, murine EPO encoding GC-rich mRNA and murine EPO encoding A-rich mRNA.

Figure 2:
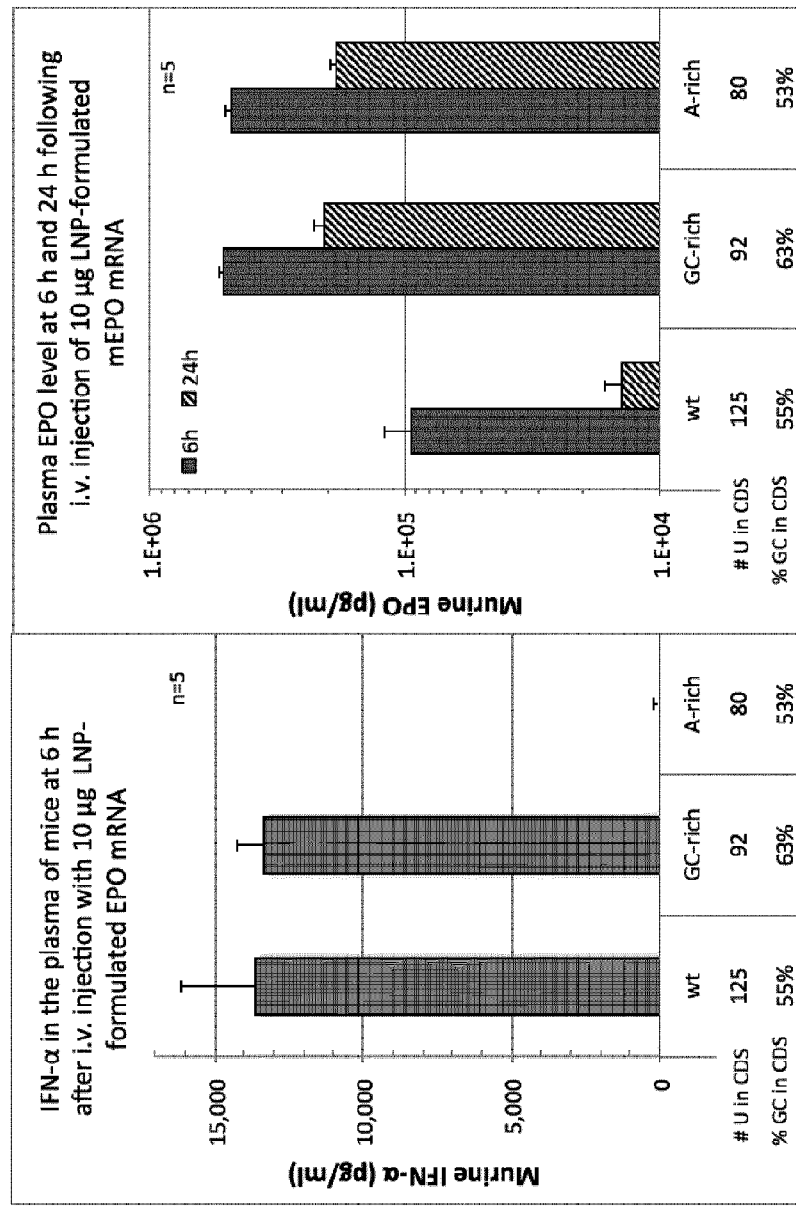
FIG. 2 shows levels of EPO & IFN alpha (IFN-α) in plasma at 6/24 h following injection of 10 μg LNP-formulated murine EPO mRNA, which were prepared according to example 2. The lowest level of IFN-α was induced by the A-rich mRNA that contained the lowest number of uridines. The A-rich RNA translated more efficiently and 5-times more EPO was produced from it compared to the wt EPO RNA. These results demonstrate direct correlation between the U-content of the RNA and its immunogenicity, as the wt RNA with the highest U content induced the most IFN-α, while the A-rich mRNA that contained the lowest number of uridine induced the least IFN-α.
Figure 3:
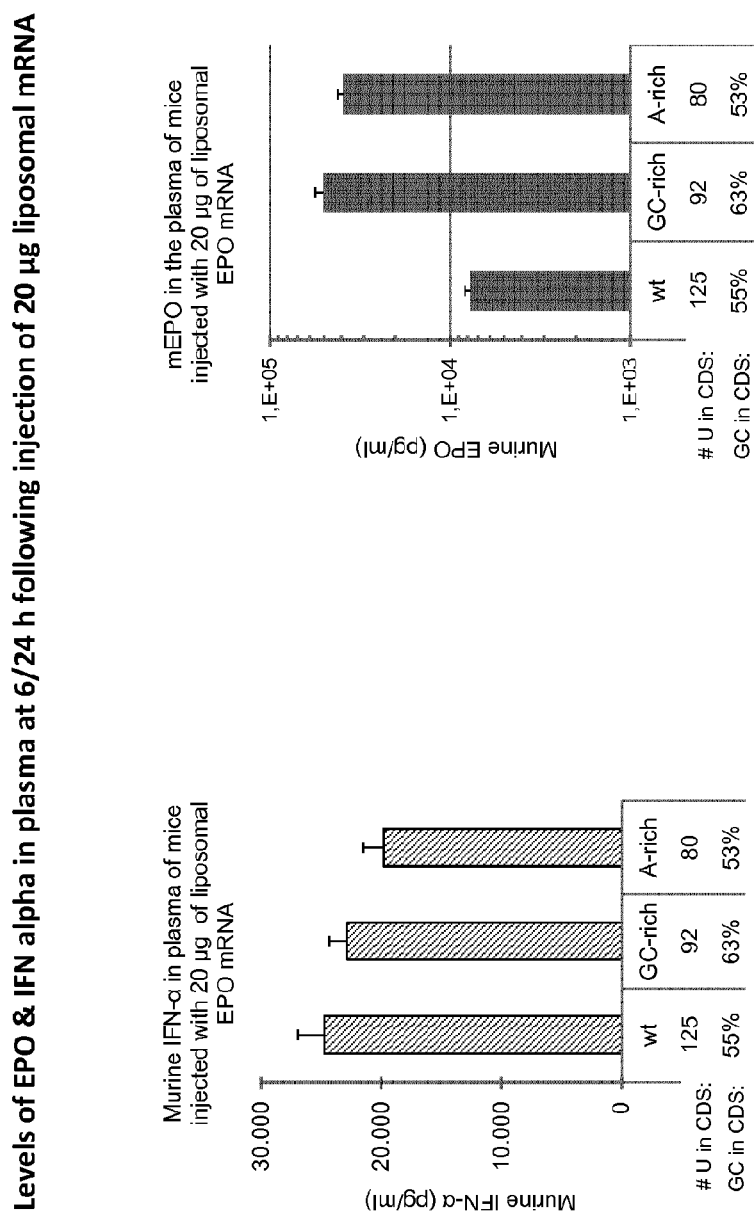
FIG. 3 shows levels of EPO & IFN alpha in plasma at 6/24 h following injection of 20 μg mRNA-liposomal formulation which were prepared according to example 4. The results were similar to those obtained with LNP-formulated mRNA since the wt RNA with the highest U content induced the most IFN-α, while the A-rich mRNA induced the least IFN-α.
Figure 4:
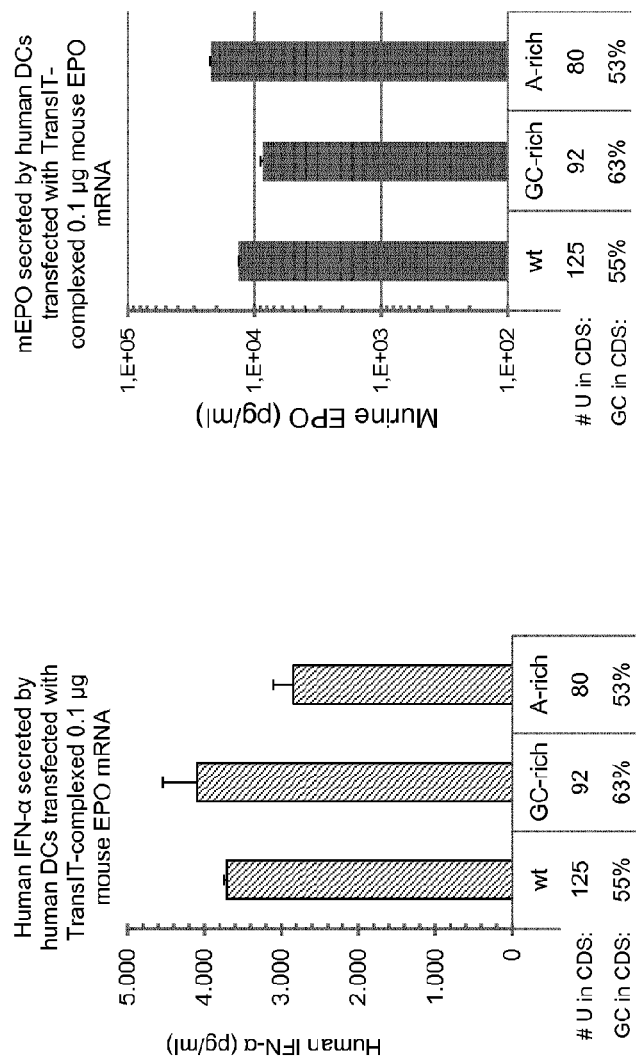
FIG. 4 shows IFN alpha induction and EPO production by human DCs transfected with 0.1 μg TransIT-complexed mouse EPO mRNA. Interferon alpha (IFN-α) and murine EPO levels were measured in the culture medium of human monocyte-derived dendritic cells at 24 h following exposure to TransIT-complexed 0.1 μg EPO mRNAs. A-rich EPO mRNA, which contained the least uridine (U) in their coding sequences (CDS) secreted the most EPO protein and induced significantly less IFN-α than the GC-rich or the wt EPO mRNAs.
Figure 6:
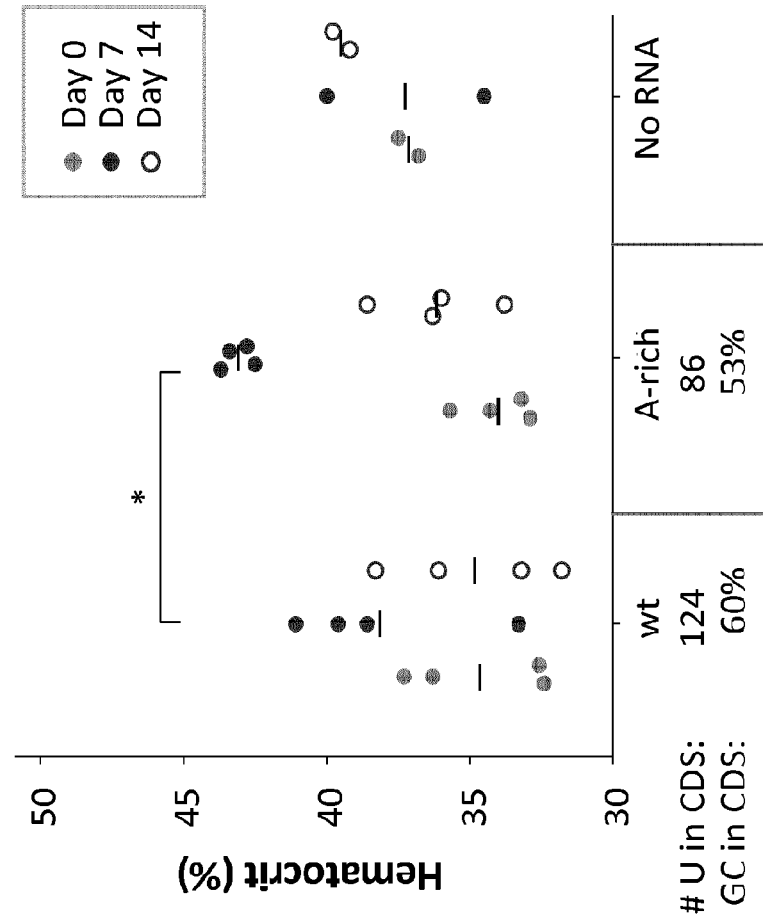
FIG. 6 shows hematocrit values obtained in mice (n=5) before (Day 0) and at day 7 and 14 after intraperitoneal injection of 3 μg of TransIT-complexed canine EPO mRNA. By day 7 hematocrits increased significantly in all mice injected with A-rich canine EPO mRNA, which contained the least uridine (U) and had the lowest GC (Guanosine & Cytidine) content in their coding sequences (CDS). At day 7 following administration of A-rich canine EPO mRNA, the hematocrits were significantly higher than in mice injected with the wt canine EPO mRNA. * Denotes p value<0.05.

Hematocrits were measured by drawing less than 20 μL of blood as described by Mahiny and Kariko (Methods Mol Biol 1428: 297-306, 2016), thus avoiding blood loss-related hematocrit increase.

Figure 7:
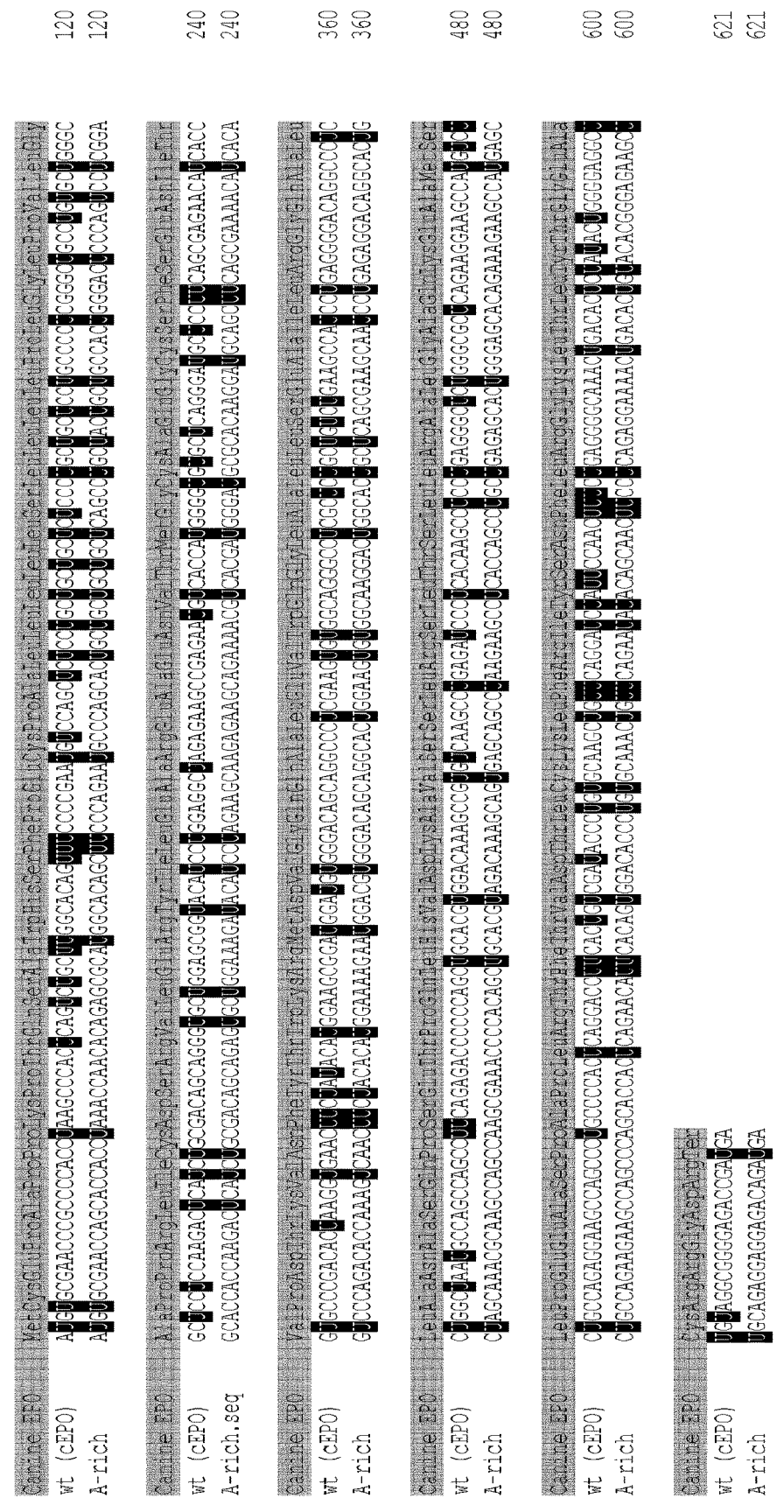

FIG. 7 shows a comparison of the uridine contents of coding sequences for canine EPO-encoding wild type mRNA and canine EPO-encoding A-rich mRNA.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "immunogenicity" refers to the ability of a particular substance, in particular RNA, to provoke an immune response in the body of an animal such as a human.

In other words, immunogenicity is the ability to induce a humoral and/or cell mediated immune response. Unwanted immunogenicity includes an immune response by an organism against a therapeutic substance such as a drug. This reaction may inactivate the therapeutic effects of the treatment and may induce adverse effects.

The RNA described herein which is modified by reducing the U content is significantly less immunogenic than an unmodified RNA molecule containing more U. In one embodiment, the modified RNA is at least 5% less immunogenic than its unmodified counterpart. In another embodiment, immunogenicity is reduced by at least 10%. In another embodiment, immunogenicity is reduced by at least 20%. In another embodiment, immunogenicity is reduced by at least 30%. In another embodiment, immunogenicity is reduced by at least 40%. In another embodiment, immunogenicity is reduced by at least 50%. In another embodiment, immunogenicity is reduced by at least 60%. In another embodiment, immunogenicity is reduced by at least 70%. In another embodiment, immunogenicity is reduced by at least 80%. In another embodiment, immunogenicity is reduced by at least 90%. In another embodiment, immunogenicity is removed or essentially removed, i.e. reduced by about 100%. The relative immunogenicity of the modified RNA and its unmodified counterpart may be determined by determining the quantity of the unmodified RNA required to elicit the same result to the same degree (e.g. expression of the same amount of protein) as a given quantity of the modified RNA. For example, if twice as much unmodified RNA is required to elicit the same response, then the modified RNA is 50% less immunogenic than the unmodified RNA. In another embodiment, the relative immunogenicity of the modified RNA and its unmodified counterpart is determined by determining the quantity of cytokine (e.g. IL-12, IFN-α, TNF-α, RANTES, MIP-1α or β, IL-6, IFN-β, or IL-8) secreted in response to administration of the modified RNA, relative to the same quantity of the unmodified RNA. For example, if one-half as much cytokine is secreted, then the modified RNA is 50% less immunogenic than the unmodified RNA.

"Significantly less immunogenic" refers to a detectable decrease in immunogenicity. In another embodiment, the term refers to a decrease such that an effective amount of the RNA can be administered or repeatedly administered without triggering a detectable immune response. In another embodiment, the term refers to a decrease such that the RNA can be repeatedly administered without eliciting an immune response sufficient to detectably reduce expression of the peptide or protein encoded by the RNA. In another embodiment, the decrease is such that the RNA can be repeatedly administered without eliciting an immune response sufficient to eliminate expression of the peptide or protein encoded by the RNA.

Terms such as "decreasing", "reducing" or "inhibiting" relate to the ability to cause an overall decrease, preferably of 5% or greater, 10% or greater, 20% or greater, more preferably of 50% or greater, and most preferably of 75% or greater, in the level. This also includes a complete or essentially complete decrease, i.e. a decrease to zero or essentially to zero.

Terms such as "increasing", "enhancing", or "prolonging" preferably relate to an increase, enhancement, or prolongation by about at least 10%, preferably at least 20%, preferably at least 30%, preferably at least 40%, preferably at least 50%, preferably at least 80%, preferably at least 100%, preferably at least 200% and in particular at least 300%. These terms may also relate to an increase, enhancement, or prolongation from zero or a non-measurable or non-detectable level to a level of more than zero or a level which is measurable or detectable.

As demonstrated herein, immunogenicity of RNA can be decreased by reducing the U content of the RNA, i.e. reducing the percentage of U nucleosides in the RNA. Reducing the U content of the RNA can be accomplished by eliminating U nucleosides from the nucleotide sequence of the RNA and/or by substituting U nucleosides by nucleosides other than U in the nucleotide sequence of the RNA.

"Eliminating U nucleosides from the nucleotide sequence of the RNA" means that U nucleosides are deleted from an RNA sequence. In one embodiment, U nucleosides are eliminated from the non-coding regions of an mRNA molecule. In one embodiment, the U nucleosides are eliminated from the 5' untranslated region (UTR) and/or the 3' UTR of an mRNA molecule. In one embodiment of the invention, at least 5%, at least 10%, at least 20%, at least 30%, at least 40%, at least 50%, at least 60%, or at least 70% of the U nucleosides are eliminated.

"Substituting U nucleosides by nucleosides other than U in the nucleotide sequence of the RNA" means that U nucleosides are deleted from an RNA sequence and the same number of nucleosides other than U are inserted, e.g. in place of the deleted U nucleosides. Thus, "substituting U nucleosides by nucleosides other than U in the nucleotide sequence of the RNA" means that the U content is reduced without removing nucleotides and thus, reducing the number of nucleotides in the RNA. U nucleosides may be substituted in the non-coding regions and/or coding regions of an mRNA molecule. In one embodiment, U nucleosides are substituted in the coding regions of an mRNA molecule. In one embodiment, the U content is reduced by substituting one codon encoding a particular amino acid by another codon encoding the same or a related amino acid, preferably the same amino acid, and containing less U. The degeneracy of the genetic code will allow the number of U nucleosides that are present in the non-modified sequence to be reduced, while maintaining the same coding capacity.

It is preferred according to the invention that the nucleotide sequence of the RNA is modified by reducing the U content in the coding region of the RNA by substituting U containing codons by other codons encoding the same amino acids but comprising fewer and preferably no U nucleosides so that the amino acid sequence of the peptide or protein encoded by the modified RNA is identical to the amino acid sequence of the peptide or protein encoded by the non-modified RNA. In one particularly preferred embodiment, the U content is reduced to the highest extent possible.

Depending on which amino acid is encoded by a codon, several different possibilities for modification of RNA sequences may be possible. In the case of amino acids encoded by codons that comprise exclusively A, C or G, no modification would be necessary to reduce the U content. In other cases, codons which comprise U nucleosides can be altered by simply substituting other codons that encode the same amino acids but that do not comprise U nucleosides or comprise fewer U nucleosides. For example:

the codons for Arg can be altered to AGA, AGG, CGC, CGA or CGG, preferably AGA instead of CGU.

the codons for Gly can be altered to GGC, GGA or GGG, preferably GGA instead of GGU.

the codons for Pro can be altered to CCC, CCA or CCG, preferably CCA instead of CCU.

the codons for Thr can be altered to ACC, ACA or ACG, preferably ACA instead of ACU.

the codons for Ala can be altered to GCC, GCA or GCG, preferably GCA instead of GCU.

the codons for Leu can be altered to CUC, CUA or CUG, preferably CUG or CUC instead of UUA, UUG or CUU.

the codons for Ile can be altered to AUC or AUA, preferably AUC instead of AUU.

the codons for Val can be altered to GUC, GUA or GUG, preferably GUG instead of GUU.

the codons for Ser can be altered to UCC, UCA, UCG or AGU instead of UCU, preferably the codons for Ser can be altered to AGC instead of UCU, UCC, UCA, UCG or AGU.

the codons for Phe can be altered to UUC instead of UUU.

the codons for Asn can be altered to AAC instead of AAU.

the codons for His can be altered to CAC instead of CAU.

the codons for Tyr can be altered to UAC instead of UAU.

the codons for Asp can be altered to GAC instead of GAU.

the codons for Cys can be altered to UGC instead of UGU.

However, there are instances in which the U content of particular codons cannot be altered by sequence changes and still encode the same amino acid. For instance:

Met-AUG

Stop-UAA, UAG or UGA

Trp-UGG

In a one embodiment of the invention, at least 5%, at least 10%, at least 20%, at least 30%, at least 40%, at least 50%, at least 60%, at least 70%, at least 80%, at least 90% or 100% of the codons which comprise U nucleosides and can be substituted by other codons that encode the same amino acids but that do not comprise U nucleosides or comprise fewer U nucleosides are substituted by other codons that encode the same amino acids but that do not comprise U nucleosides or comprise fewer U nucleosides. In one particularly preferred embodiment, at least as many of the codons which comprise U nucleosides and can be substituted by other codons that encode the same amino acids but that do not comprise U nucleosides or comprise fewer U nucleosides are substituted by other codons that encode the same amino acids but that do not comprise U nucleosides or comprise fewer U nucleosides such that immunogenicity of the RNA is decreased.

In one embodiment of the invention, at least 5%, at least 10%, at least 20%, at least 30%, at least 40%, at least 50%, at least 60%, or at least 70% of the U nucleosides are eliminated by substitution. It is preferred according to the invention that the U content of the RNA is reduced by at least 5%, preferably at least 10%, preferably at least 15%, preferably at least 20%, preferably at least 30% or preferably at least 40% and up to 80%, preferably up to 70%, preferably up to 60%, or preferably up to 50%. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

It is preferred according to the invention that in the modified RNA having a reduced U content, the GC content is not significantly increased compared to the non-modified RNA. In this respect, "not significantly increased" means that the GC content is increased by at most 10%, preferably at most 5%, more preferably at most 3%, 2% or 1%. In one particularly preferred embodiment, the GC content is not increased, i.e. it remains essentially constant, or is reduced. In this respect, "reduced GC content" preferably means that the GC content is reduced by at least 1%, preferably at least 2%, preferably at least 3%, more preferably at least 4%, at least 5%, at least 6%, at least 7%, at least 8%, at least 9% or at least 10%. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

It is preferred according to the invention that in the modified RNA having a reduced U content, the A content is increased compared to the non-modified RNA. In this respect, "increased A content" preferably means that the A content is increased by at least 1%, preferably at least 3%, preferably at least 5%, preferably at least 10%, more preferably at least 15%, at least 20%, at least 25%, at least 30%, at least 35%, at least 37%, or at least 40%. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

An increase in A content (and non significant increase in GC content, preferably constant GC content or reduction in GC content) can be achieved by altering codons which comprise U nucleosides by substituting—at least partially—other codons that encode the same amino acids but that do not comprise U nucleosides or comprise fewer U nucleosides and have a high A content and a low GC content. For example:

the codons for Arg can be altered to AGA instead of CGU.

the codons for Gly can be altered to GGA instead of GGU.

the codons for Pro can be altered to CCA instead of CCU.

the codons for Thr can be altered to ACA instead of ACU.

the codons for Ala can be altered to GCA instead of GCU.

Alternatively or additionally, an increase in A content (and non significant increase in GC content, preferably constant GC content or reduction in GC content) can be achieved by altering codons by substituting—at least partially—other codons that encode the same amino acids, do not comprise more U nucleosides—preferably no U nucleosides as the substituted codons—and have a high A content and a low GC content. For example:

the codons for Arg can be altered to AGA instead of CGG, AGG, CGC and CGA.

the codons for Gly can be altered to GGA instead of GGC and GGG.

the codons for Pro can be altered to CCA instead of CCC and CCG.

the codons for Thr can be altered to ACA instead of ACC and ACG.

the codons for Ala can be altered to GCA instead of GCC and GCG.

the codons for Glu can be altered to GAA instead of GAG.

the codons for Lys can be altered to AAA instead of AAG.

In one particularly preferred embodiment, the modified RNA having a reduced U content is A-rich (or A-enriched compared to the non-modified RNA, i.e. its A content is increased).

The term "A-rich" as used herein refers to nucleic acid molecules with an A content of more than 25%. In particular aspects, the A-rich nucleic acid comprises about 30% A to about 37% A, and in additional aspects, the A-rich nucleic acid comprises greater than about 26% A, greater than about 27% A, greater than about 28% A, greater than about 29% A, greater than about 30% A, greater than about 31% A, greater than about 32% A, greater than about 33% A, greater than about 34% A, greater than about 35% A, greater than about 36% A, and so forth. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

In one embodiment, an A-rich RNA according to the invention has a GC content of less than about 60%. In another embodiment, an A-rich RNA has a GC content of less than about 55%. In another embodiment, an A-rich RNA has a GC content of less than about 54%. In another embodiment, an A-rich RNA has a GC content of less than about 53%. In another embodiment, an A-rich RNA has a GC content of less than about 52%. In another embodiment, an A-rich RNA has a GC content of less than about 51%. In another embodiment, an A-rich RNA has a GC content of less than about 50%. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

The term "GC-rich" as used herein refers to nucleic molecules with a G+C content of more than 50%. In particular aspects, the GC-rich nucleic acid comprises about 60% GC to about 75% GC, and in additional aspects, the GC-rich nucleic acid comprises greater than about 55% GC, greater than about 60% GC, greater than about 61% GC, greater than about 62% GC, greater than about 63% GC, greater than about 64% GC, greater than about 65% GC, greater than about 66% GC, greater than about 67% GC, greater than about 68% GC, greater than about 69% GC, greater than about 70% GC, and so forth. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

In one embodiment, GC-rich RNA according to the invention has an A content of less than about 30%. In another embodiment, a GC-rich RNA has an A content of less than about 25%. In another embodiment, a GC-rich RNA has an A content of less than about 24%. In another embodiment, a GC-rich RNA has an A content of less than about 23%. In another embodiment, a GC-rich RNA has an A content of less than about 22%. In another embodiment, a GC-rich RNA has an A content of less than about 21%. In another embodiment, a GC-rich RNA has an A content of less than about 20%. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

As used herein, the term "U content" refers to the amount of nucleosides of a particular RNA molecule or RNA sequence that are uridine (U) typically expressed as a percent. Where the sequence of particular RNA is known, the U content can be determined using the formula:

$$\frac{U}{A+U+G+C} \times 100$$

wherein G, C, A and U refer to the number of each residue in the particular RNA molecule or RNA sequence, to provide a percent U content. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

As used herein, the term "A content" refers to the amount of nucleosides of a particular RNA molecule or RNA sequence that are adenosine (A) typically expressed as a percent. Where the sequence of particular RNA is known, the A content can be determined using the formula:

$$\frac{A}{A+U+G+C} \times 100$$

wherein G, C, A and U refer to the number of each residue in the particular RNA molecule or RNA sequence, to provide a percent A content. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

As used herein, the term "G+C content" or "GC content" refers to the amount of nucleosides of a particular RNA molecule or RNA sequence that are either guanosine (G) or cytidine (C) typically expressed as a percent. Where the sequence of particular RNA is known, the G+C content can be determined using the formula:

$$\frac{G+C}{A+U+G+C} \times 100$$

wherein G, C, A and U refer to the number of each residue in the particular RNA molecule or RNA sequence, to provide a percent GC content. If the nucleotide sequence of the RNA is only modified by reducing the U content in the coding region of the RNA by substituting U containing codons by other codons encoding the same amino acids but comprising fewer and preferably no U nucleosides the above may relate to the nucleotide sequence of the coding region only.

There are a variety of different methods that can be used to substitute nucleosides and, in particular codons. For example, base substitutions can be made in the DNA template used for making an RNA by standard site-directed mutagenesis (See, for example, Molecular Cloning A Laboratory Manual, 2nd Ed., ed. by Sambrook, Fritsch and Maniatis (Cold Spring Harbor Laboratory Press: 1989 or 1991 edition). Alternatively, an entire RNA can be synthesized from DNA template enzymatically using standard in vitro transcription techniques. In the case of enzymatically synthesized RNAs it may be desirable to make other modifications, e.g. modifications to enhance RNA stability. For example, a cap can be added to the synthetized RNA post-transcriptionally using capping enzymes or during transcription. Likewise, a poly A tail can be added post-transcriptionally using enzymes, e.g., with poly A polymerase or during transcription from the DNA template.

It should be understood that in addition to the sequence changes described above, other sequence changes can be made in the RNA, e.g. the subject RNA can be made more nuclease resistant by removing nuclease sensitive motifs. Certain RNAs are naturally unstable in a cell, and this is normally due to the existence of destabilizing sequence motifs within such unstable RNAs that are recognized by nucleases. If such sequences exist in a RNA, they can be eliminated, replaced or modified by standard genetic engineering.

The term "nucleoside" relates to compounds which can be thought of as nucleotides without a phosphate group. While a nucleoside is a nucleobase linked to a sugar (e.g. ribose or deoxyribose), a nucleotide is composed of a nucleoside and one or more phosphate groups. Examples of nucleosides include cytidine, uridine, adenosine, and guanosine.

Uridine is a glycosylated pyrimidine-analog containing uracil attached to a ribose ring (or more specifically, a ribofuranose) via a β-N1-glycosidic bond. It is one of the five standard nucleosides which make up nucleic acids, the others being adenosine, thymidine, cytidine and guanosine. The five nucleosides are commonly abbreviated to their one letter codes U, A, T, C and G, respectively. However, thymidine is more commonly written as "dT" ("d" represents "deoxy") as it contains a 2'-deoxyribofuranose moiety rather than the ribofuranose ring found in uridine. This is because thymidine is found in deoxyribonucleic acid (DNA) and not ribonucleic acid (RNA). Conversely, uridine is found in RNA and not DNA. The remaining three nucleosides may be found in both RNA and DNA. In RNA, they would be represented as A, C and G, whereas in DNA they would represented as dA, dC and dG.

According to the invention, a nucleic acid or nucleic acid molecule refers to a nucleic acid which is preferably deoxyribonucleic acid (DNA) or ribonucleic acid (RNA). According to the invention, nucleic acids comprise genomic DNA, cDNA, mRNA, recombinantly prepared and chemically synthesized molecules. According to the invention, a nucleic acid may be in the form of a single-stranded or double-stranded and linear or covalently closed circular molecule. The term "nucleic acid" according to the invention also comprises a chemical derivatization of a nucleic acid on a nucleotide base, on the sugar or on the phosphate, and nucleic acids containing non-natural nucleotides and nucleotide analogs.

In the context of the present invention, the term "RNA" relates to a molecule which comprises ribonucleotide residues and preferably being entirely or substantially composed of ribonucleotide residues. The term "ribonucleotide" relates to a nucleotide with a hydroxyl group at the 2'-position of a β-D-ribofuranosylgoup. The term "RNA" comprises double-stranded RNA, single stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs, particularly analogs of naturally-occurring RNAs. According to the invention, RNA includes and preferably relates to mRNA. RNA such as mRNA described herein may have a length of between about 500 to about 10000, 5000 or 2000 nucleotides. In another embodiment, the RNA has a length of between about 500 to about 1000 nucleotides. In another embodiment, the RNA is greater than 30 nucleotides in length. In another embodiment, the RNA is greater than 50 nucleotides in length. In another embodiment, the length is at least 60 nucleotides. In another embodiment, the length is at least 80 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides.

As used herein, the term "RNA" includes chemically modified, non-naturally occurring RNA. Such chemical modifications may render the RNA molecule more resistant to nucleases than a naturally occurring RNA molecule. Exemplary modifications to a nucleic acid sequence of an RNA molecule include, for example, the modification of a base, e.g., the chemical modification of a base. The term "chemical modification" as used herein, includes modifications which introduce chemistries which differ from those seen in naturally occurring RNA. For example, chemical modifications include covalent modifications such as the introduction of modified nucleotides, e.g., nucleotide analogs, or the inclusion of pendant groups which are not naturally found in RNA molecules. Such modifications include, but are not limited to pseudouridine, 1-methylpseudouridine, 1-methyl-3-(3-amino-3-carboxypropyl) pseudouridine, 2'-O-methylpseudouridine, 5-methyldihydrouridine, 5-methylcytidine, 5-methyluridine, N6-methyladenosine, 2-thiouridine, 2'-O-methyluridine, 1-methyladenosine, 2-methyladenosine, 2'-O-methyladenosine, 2-methylthio-N6-methyladenosine, inosine, 1-methylinosine, 3-methylcytidine, 2'-O-methylcytidine, 2-thiocytidine, N4-acetylcytidine, 5-formylcytidine, 5,2'-O-dimethylcytidine, 1-methylguanosine, N2-methylguanosine, 7-methylguanosine, 2'-O-methylguanosine, N2,N2-dimethylguanosine, dihydrouridine, 5,2'-O-dimethyluridine, 4-thiouridine, 5-methyl-2-thiouridine, 2-thio-2'-O-methyluridine, 5-hydroxyuridine, 5-methoxyuridine and 3-methyluridine.

The term "mRNA" means "messenger-RNA" and relates to a transcript which is generated by using a DNA template and encodes a peptide or protein. Typically, mRNA comprises a 5' UTR, a protein coding region, a 3' UTR, and a poly(A) sequence and may also comprise a 5' cap. Several regions of the mRNA molecule are not translated into protein including the 5' cap, 5' UTR, 3' UTR, and the poly(A) sequence.

The term "untranslated region" (or UTR) refers to either of two sections, one on each side of a coding region on a strand of mRNA. If it is found on the 5' side, it is called the 5' UTR, or if it is found on the 3' side, it is called the 3' UTR.

The term "5' untranslated region" relates to a region which is located at the 5' end of a gene, upstream from the initiation codon of a protein-encoding region, and which is transcribed but is not translated into an amino acid sequence, or to the corresponding region in an RNA molecule. This region is important for the regulation of translation of a transcript by differing mechanisms in viruses, prokaryotes and eukaryotes. While called untranslated, the 5' UTR or a portion of it is sometimes translated into a protein product. This product can then regulate the translation of the main coding sequence of the mRNA. In many other organisms, however, the 5' UTR is completely untranslated, instead forming complex secondary structure to regulate translation. The 5' UTR begins at the transcription start site and ends one nucleotide (nt) before the initiation sequence (usually AUG) of the coding region. In prokaryotes, the length of the 5' UTR tends to be 3-10 nucleotides long while in eukaryotes it tends to be anywhere from 100 to several thousand nucleotides long. The elements of a eukaryotic and prokaryotic 5' UTR differ greatly. The prokaryotic 5' UTR contains a ribosome binding site (RBS), also known as the Shine Dalgarno sequence (AGGAGGU) which is usually 3-10 nucleotides upstream from the initiation codon. Meanwhile the eukaryotic 5' UTR contains the Kozak consensus sequence (ACCAUGG), which contains the initiation codon.

The term "3' untranslated region" relates to a region which is located at the 3' end of a gene, downstream of the termination codon of a protein-encoding region, and which is transcribed but is not translated into an amino acid sequence, or to the corresponding region in an RNA molecule. Regulatory regions within the 3' untranslated region can influence polyadenylation, translation efficiency, localization, and stability of the mRNA. The 3' UTR contains both binding sites for regulatory proteins as well as microRNAs (miRNAs). The 3' untranslated region typically extends from the termination codon for a translation product to the poly(A) sequence which is usually attached after the transcription process. The 3' untranslated regions of mammalian mRNA typically have a homology region known as the AAUAAA hexanucleotide sequence. This sequence is presumably the poly(A) attachment signal and is frequently located from 10 to 30 bases upstream of the poly(A) attachment site.

According to the invention, a first polynucleotide region is considered to be located downstream of a second polynucleotide region, if the 5' end of said first polynucleotide region is the part of said first polynucleotide region closest to the 3' end of said second polynucleotide region.

Polyadenylation is the addition of a poly(A) sequence or tail to a primary transcript RNA. The poly(A) sequence consists of multiple adenosine monophosphates residues called adenylates. In other words, it is a stretch of RNA that has only adenine bases. In eukaryotes, polyadenylation is part of the process that produces mature messenger RNA (mRNA) for translation. It, therefore, forms part of the larger process of gene expression. The process of polyadenylation begins as the transcription of a gene finishes, or terminates. The 3' most segment of the newly made pre-mRNA is first cleaved off by a set of proteins; these proteins then synthesize the poly(A) sequence at the RNA's 3' end. The poly(A) sequence is important for the nuclear export, translation, and stability of mRNA. The sequence is shortened over time, and, when it is short enough, the mRNA is enzymatically degraded.

The terms "polyadenyl sequence", "poly(A) sequence" or "poly(A) tail" refer to a sequence of adenylate residues which is typically located at the 3' end of an RNA molecule. The invention provides for such a sequence to be attached during RNA transcription by way of a DNA template on the basis of repeated thymidylate residues in the strand complementary to the coding strand, whereas said sequence is normally not encoded in the DNA but is attached to the free 3' end of the RNA by a template-independent RNA polymerase after transcription in the nucleus. According to the invention, in one embodiment, a poly(A) sequence has at least 20, preferably at least 40, preferably at least 80, preferably at least 100 and preferably up to 500, preferably up to 400, preferably up to 300, preferably up to 200, and in particular up to 150 A nucleotides, preferably consecutive A nucleotides, and in particular about 120 A nucleotides. The term "A nucleotides" or "A" refers to adenylate residues.

The term "5' cap" refers to a cap structure found on the 5' end of an mRNA molecule and generally consists of a guanosine nucleotide connected to the mRNA via an unusual 5' to 5' triphosphate linkage. In one embodiment, this guanosine is methylated at the 7-position. The term "conventional 5' cap" refers to a naturally occurring RNA 5' cap, preferably to the 7-methylguanosine cap (m7G). In the context of the present invention, the term "5' cap" includes a 5' cap analog that resembles the RNA cap structure and is modified to possess the ability to stabilize RNA if attached thereto, preferably in vivo and/or in a cell. Providing an RNA with a 5' cap or 5' cap analog may be achieved by in vitro transcription of a DNA template in the presence of said 5' cap or 5' cap analog, wherein said 5' cap is co-transcriptionally incorporated into the generated RNA strand, or the RNA may be generated, for example, by in vitro transcription, and the 5' cap may be generated post-transcriptionally using capping enzymes, for example, capping enzymes of vaccinia virus.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

In particular embodiments, the RNA according to the invention comprises a population of different RNA molecules, e.g. a mixture of different RNA molecules optionally encoding different peptides and/or proteins, whole-cell RNA, an RNA library, or a portion of thereof, e.g. a library of RNA molecules expressed in a particular cell type, such as undifferentiated cells, in particular stem cells such as embryonic stem cells, or a fraction of the library of RNA molecules such as RNA with enriched expression in undifferentiated cells, in particular stem cells such as embryonic stem cells relative to differentiated cells. Thus, according to the invention, the term "RNA" may include a mixture of RNA molecules, whole-cell RNA or a fraction thereof, which may be obtained by a process comprising the isolation of RNA from cells and/or by recombinant means, in particular by in vitro transcription.

According to the invention, the term "gene" refers to a particular nucleic acid sequence which is responsible for producing one or more cellular products and/or for achieving one or more intercellular or intracellular functions. More specifically, said term relates to a DNA section which comprises a nucleic acid coding for a specific protein or a functional or structural RNA molecule.

RNA can be isolated from cells, can be made from a DNA template, or can be chemically synthesized using methods known in the art. In preferred embodiment, RNA is synthesized in vitro from a DNA template. In one particularly preferred embodiment, RNA, in particular mRNA is generated by in vitro transcription from a DNA template. The in vitro transcription methodology is known to the skilled person. For example, there is a variety of in vitro transcription kits commercially available. In one particularly preferred embodiment, RNA is in vitro transcribed RNA (IVT RNA).

Preferably the RNA described herein is eukaryotic, preferably mammalian in origin. In preferred embodiments, the RNA comprises characteristics of eukaryotic mRNA, e.g., the presence of a 5' cap, and/or the presence of a poly(A) sequence.

In a preferred embodiment, a nucleic acid molecule according to the invention is a vector. The term "vector" is used here in its most general meaning and comprises any intermediate vehicles for a nucleic acid which, for example, enable said nucleic acid to be introduced into prokaryotic and/or eukaryotic host cells and, where appropriate, to be integrated into a genome. Such vectors are preferably replicated and/or expressed in the cell. Vectors comprise plasmids, phagemids or virus genomes. The term "plasmid", as used herein, generally relates to a construct of extrachromosomal genetic material, usually a circular DNA duplex, which can replicate independently of chromosomal DNA.

The nucleic acids described herein may be recombinant and/or isolated molecules.

An "isolated molecule" as used herein, is intended to refer to a molecule which has been separated from its natural environment and preferably is substantially free of other molecules such as other cellular material. The term "isolated nucleic acid" means according to the invention that the nucleic acid has been (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid available to manipulation by recombinant DNA techniques.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide, protein or nucleic acid that is present in an organism (including viruses) and can be isolated from a source in nature and which has not been intentionally modified by man in the laboratory is naturally occurring.

As a nucleic acid, in particular RNA, for expression of more than one peptide or protein, either of a nucleic acid type in which the different peptides or proteins are encoded in different nucleic acid molecules or a nucleic acid type in which the peptides or proteins are encoded in the same nucleic acid molecule can be used.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable.

According to the invention, terms such as "RNA expression", "expressing RNA", or "expression of RNA" relate to the production of peptide or protein encoded by the RNA. Preferably, such terms relate to the translation of RNA so as to express, i.e. produce, peptide or protein encoded by the RNA.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, RNA preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide or protein.

The term "expression control sequence" comprises according to the invention promoters, ribosome-binding sequences and other control elements which control transcription of a gene or translation of the derived RNA. In particular embodiments of the invention, the expression control sequences can be regulated. The precise structure of expression control sequences may vary depending on the species or cell type but usually includes 5' untranscribed and 5' and 3' untranslated sequences involved in initiating transcription and translation, respectively, such as TATA box, capping sequence, CAAT sequence and the like. More specifically, 5' untranscribed expression control sequences include a promoter region which encompasses a promoter sequence for transcription control of the functionally linked gene. Expression control sequences may also include enhancer sequences or upstream activator sequences.

The nucleic acid sequences specified herein, in particular transcribable and coding nucleic acid sequences, may be combined with any expression control sequences, in particular promoters, which may be homologous or heterologous to said nucleic acid sequences, with the term "homologous" referring to the fact that a nucleic acid sequence is also functionally linked naturally to the expression control sequence, and the term "heterologous" referring to the fact that a nucleic acid sequence is not naturally functionally linked to the expression control sequence.

The term "promoter" or "promoter region" refers to a DNA sequence upstream (5') of the coding sequence of a gene, which controls expression of said coding sequence by providing a recognition and binding site for RNA polymerase. The promoter region may include further recognition or binding sites for further factors involved in regulating transcription of said gene. A promoter may control transcription of a prokaryotic or eukaryotic gene. A promoter may be "inducible" and initiate transcription in response to an inducer, or may be "constitutive" if transcription is not controlled by an inducer. An inducible promoter is expressed only to a very small extent or not at all, if an inducer is absent. In the presence of the inducer, the gene is "switched on" or the level of transcription is increased. This is usually mediated by binding of a specific transcription factor.

Examples of promoters preferred according to the invention are promoters for SP6, T3 or T7 polymerase.

Decreased immunogenicity of RNA according to the invention may result in enhanced expression of said RNA.

Terms such as "enhancement of expression", "enhanced expression" or "increased expression" mean in the context of the present invention that the amount of peptide or protein expressed by a given number of RNA molecules is higher than the amount of peptide or protein expressed by the same number of RNA molecules, wherein expression of the RNA molecules is performed under the same conditions except the condition which results in the enhanced or increased expression of the RNA. In this context, "same conditions", for example, refer to a situation wherein RNA sequences encoding the same peptide or protein are administered to a subject by the same means and the amount of peptide or protein is measured by the same means. The amount of peptide or protein may be given in moles, or by weight, e.g. in grams, or by mass or by polypeptide activity, e.g. if the peptide or protein is an enzyme it may be given as catalytic activity or if the peptide or protein is an antibody or antigen or a receptor it may be given as binding affinity. In one embodiment, terms such as "enhancement of expression", "enhanced expression" or "increased expression" mean in the context of the present invention that the amount of peptide or protein expressed by a given number of RNA molecules and within a given period of time is higher than the amount of peptide or protein expressed by the same number of RNA molecules and within the same period of time. For example, the maximum value of peptide or protein expressed by a given number of RNA molecules at a particular time point may be higher than the maximum value of peptide or protein expressed by the same number of RNA molecules. In other embodiments, the maximum value of peptide or protein expressed by a given number of RNA molecules does not need to be higher than the maximum value of peptide or protein expressed by the same number of RNA molecules, however, the average amount of peptide or protein expressed by the given number of RNA molecules within a given period of time may be higher than the average amount of peptide or protein expressed by the same number of RNA molecules. The latter cases are referred to herein as "higher level of expression" or "increased level of expression" and relate to higher maximum values of expression and/or higher average values of expression. Alternatively or additionally, terms such as "enhancement of expression", "enhanced expression" or "increased expression" mean in the context of the present invention also that the time in which peptide or protein is expressed by RNA molecules may be longer. Thus, in one embodiment, terms such as "enhancement of expression", "enhanced expression" or "increased expression" mean in the context of the present invention also that the amount of peptide or protein expressed by a given number of RNA molecules is higher than the amount of peptide or protein expressed by the same number of RNA molecules since the period of time in which the RNA is stably present and expressed is longer than the period of time in which the same number of RNA molecules is stably present and expressed. These cases are referred to herein also as "increased duration of expression". Preferably, such longer time periods refer to expression for at least 48 h, preferably for at least 72 h, more preferably for at least 96 h, in particular for at least 120 h or even longer following administration of RNA or following the first administration (e.g. in case of repeated administrations) of RNA.

The level of expression and/or duration of expression of RNA may be determined by measuring the amount, such as the total amount expressed and/or the amount expressed in a given time period, and/or the time of expression of the peptide or protein encoded by the RNA, for example, by using an ELISA procedure, an immunohistochemistry procedure, a quantitative image analysis procedure, a Western Blot, mass spectrometry, a quantitative immunohistochemistry procedure, or an enzymatic assay.

Preferably, according to the invention, following administration of RNA to a subject, the RNA is to be taken up by cells of the subject, i.e. cells of the subject are to be transfected with the RNA, for expression of the peptide or protein encoded by the RNA.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded peptide or protein.

According to the present invention, any technique useful for introducing, i.e. transferring or transfecting, nucleic acids into cells in vitro may be used. Preferably, nucleic acid is transfected into cells by standard techniques. Such techniques include electroporation, lipofection and microinjection. In one particularly preferred embodiment of the present invention, nucleic acid is introduced into cells by electroporation. Electroporation or electropermeabilization relates to a significant increase in the electrical conductivity and permeability of the cell plasma membrane caused by an externally applied electrical field. It is usually used in molecular biology as a way of introducing some substance into a cell.

According to the invention it is preferred that introduction of nucleic acid encoding a protein or peptide into cells or uptake of nucleic acid encoding a protein or peptide by cells results in expression of said protein or peptide. The cell may express the encoded peptide or protein intracellularly (e.g. in the cytoplasm and/or in the nucleus), may secrete the encoded peptide or protein, or may express it on the surface.

According to the present invention, the administration of a nucleic acid, in particular RNA, is either achieved as naked nucleic acid or in combination with an administration reagent. Preferably, administration of nucleic acids is in the form of naked nucleic acids. Preferably, the RNA is administered in combination with stabilizing substances such as RNase inhibitors. The present invention also envisions the repeated introduction of nucleic acids into cells to allow sustained expression for extended time periods. RNA can be administered with any carriers with which RNA can be associated, e.g. by forming complexes with the RNA or forming vesicles in which the RNA is enclosed or encapsulated, resulting in increased stability of the RNA compared to naked RNA. Carriers useful according to the invention include, for example, lipid-containing carriers such as cationic lipids, liposomes, in particular cationic liposomes, and micelles. Cationic lipids may form complexes with negatively charged nucleic acids. Any cationic lipid may be used according to the invention.

According to the invention, nucleic acids may be directed to particular cells. In such embodiments, a carrier used for administering a nucleic acid to a cell (e.g. a retrovirus or a liposome) may have a bound targeting molecule. For example, a molecule such as an antibody specific to a surface membrane protein on the target cell, or a ligand for a receptor on the target cell may be incorporated into or bound to the nucleic acid carrier. If administration of a nucleic acid by liposomes is desired, proteins binding to a surface membrane protein associated with endocytosis may be incorporated into the liposome formulation in order to enable targeting and/or absorption. Such proteins include capsid proteins or fragments thereof which are specific to a particular cell type, antibodies to proteins that are internalized, proteins targeting an intracellular site, and the like.

Interferons are important cytokines characterized by antiviral, antiproliferative and immunomodulatory activities. Interferons are proteins that alter and regulate the transcription of genes within a cell by binding to interferon receptors on the regulated cell's surface, thereby preventing viral replication within the cells. The interferons can be grouped into two types. IFN-gamma is the sole type II interferon; all others are type I interferons. Type I and type II interferons differ in gene structure (type II interferon genes have three exons; type I, one), chromosome location (in humans, type II is located on chromosome-12; the type I interferon genes are linked and on chromosome-9), and the types of tissues where they are produced (type I interferons are synthesized ubiquitously, type II by lymphocytes). Type I interferons competitively inhibit each others binding to cellular receptors, while type II interferon has a distinct receptor. According to the invention, the term "interferon" or "IFN" preferably relates to type I interferons, in particular IFN-alpha and IFN-beta.

According to the invention, the term "host cell" refers to any cell which can be transformed or transfected with an exogenous nucleic acid. The term "host cell" comprises, according to the invention, prokaryotic (e.g. E.coli) or eukaryotic cells (e.g. yeast cells and insect cells). Particular preference is given to mammalian cells such as cells from humans, mice, hamsters, pigs, goats, primates. The cells may be derived from a multiplicity of tissue types and comprise primary cells and cell lines. Specific examples include keratinocytes, peripheral blood leukocytes, bone marrow stem cells and embryonic stem cells. In other embodiments, the host cell is an antigen-presenting cell, in particular a dendritic cell, a monocyte or a macrophage. A nucleic acid may be present in the host cell in a single or in several copies and, in one embodiment is expressed in the host cell.

According to the present invention, the term "peptide" comprises oligo- and polypeptides and refers to substances which comprise two or more, preferably 3 or more, preferably 4 or more, preferably 6 or more, preferably 8 or more, preferably 10 or more, preferably 13 or more, preferably 16 or more, preferably 20 or more, and up to preferably 50, preferably 100 or preferably 150, consecutive amino acids linked to one another via peptide bonds. The term "protein" refers to large peptides, preferably peptides having at least 151 amino acids, but the terms "peptide" and "protein" are used herein usually as synonyms.

The terms "peptide" and "protein" comprise according to the invention substances which contain not only amino acid components but also non-amino acid components such as sugars and phosphate structures, and also comprise substances containing bonds such as ester, thioether or disulfide bonds.

According to the present invention, a nucleic acid such as RNA may encode a peptide or protein. Accordingly, a nucleic acid such as RNA may contain a coding region (open reading frame (ORF)) encoding a peptide or protein. Said nucleic may express the encoded peptide or protein. For example, said nucleic acid may be a nucleic acid encoding and expressing an antigen or a pharmaceutically active peptide or protein such as an immunologically active compound (which preferably is not an antigen). In this respect, an "open reading frame" or "ORF" is a continuous stretch of codons beginning with a start codon and ending with a stop codon.

According to the invention, the term "RNA encoding a peptide or protein" means that the RNA, if present in the appropriate environment, preferably within a cell, can direct the assembly of amino acids to produce, i.e. express, the peptide or protein during the process of translation. Preferably, RNA according to the invention is able to interact with the cellular translation machinery allowing translation of the peptide or protein.

According to the invention, in one embodiment, RNA comprises or consists of pharmaceutically active RNA. A "pharmaceutically active RNA" may be RNA that encodes a pharmaceutically active peptide or protein.

The term "pharmaceutically active peptide or protein" includes a peptide or protein that can be used in the treatment of a subject where the expression of a peptide or protein would be of benefit, e.g., in ameliorating the symptoms of a disease or disorder. For example, a pharmaceutically active protein can replace or augment protein expression in a cell which does not normally express a protein or which misexpresses a protein, e.g., a pharmaceutically active protein can compensate for a mutation by supplying a desirable protein. In addition, a "pharmaceutically active peptide or protein" can produce a beneficial outcome in a subject, e.g., can be used to produce a protein to which vaccinates a subject against an infectious disease. Preferably, a "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., the peptide or protein elicits an immune response in a subject which may be therapeutic or partially or fully protective.

"Effective amount" or "therapeutically effective amount" (with respect to e.g. RNA, peptide or protein) refers to an amount sufficient to exert a therapeutic effect. In another embodiment, the term refers to an amount of RNA sufficient to elicit expression of a detectable amount of the peptide or protein encoded by the RNA.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also downregulate other aspects of the immune response, for example shifting the immune response away from a TH2 immune response, which is useful for treating a wide range of TH2 mediated diseases. Immunologically active compounds can be useful as vaccine adjuvants.

In one embodiment, RNA that codes for an antigen such a disease-associated antigen is administered to a mammal, in particular if treating a mammal having a disease involving the antigen is desired. The RNA is preferably taken up into the mammal's antigen-presenting cells (monocytes, macrophages, dendritic cells or other cells). An antigenic translation product of the RNA is formed and the product is displayed on the surface of the cells for recognition by T cells. In one embodiment, the antigen or a product produced by optional procession thereof is displayed on the cell surface in the context of MHC molecules for recognition by T cells through their T cell receptor leading to their activation.

The present invention also includes "variants" of the peptides, proteins, or amino acid sequences described herein.

For the purposes of the present invention, "variants" of an amino acid sequence comprise amino acid insertion variants, amino acid addition variants, amino acid deletion variants and/or amino acid substitution variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids or nucleotides that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

According to the invention, a variant of a peptide or protein preferably has a functional property of the peptide or protein from which it has been derived.

The term "disease" or "disorder" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. As used herein the term "disease" or "disorder" includes, in particular, a condition which would benefit from the expression of a peptide or protein (as described above), e.g., as demonstrated by a reduction in and/or an amelioration of symptoms.

According to the invention, the term "disease" also refers to cancer diseases. The terms "cancer disease" or "cancer" (medical term: malignant neoplasm) refer to a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e. a swelling or lesion formed by an abnormal growth of cells (called neoplastic cells or tumor cells), but some, like leukemia, do not. Examples of cancers include, but are not limited to, carcinoma, lymphoma, blastoma, sarcoma, glioma and leukemia. More particularly, examples of such cancers include bone cancer, blood cancer, lung cancer, liver cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

The term "infectious disease" refers to any disease which can be transmitted from individual to individual or from organism to organism, and is caused by a microbial agent (e.g. common cold). Examples of infectious diseases include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), and severe acute respiratory syndrome (SARS), bacterial infectious diseases, such as Legionnaire's disease (*Legionella*), sexually transmitted diseases (e.g. *chlamydia* or gonorrhea), gastric ulcer (*Helicobacter*), cholera (*Vibrio*), tuberculosis, diphtheria, infections by *E.coli*, Staphylococci, *Salmonella* or Streptococci (tetanus); infections by protozoan pathogens such as malaria, sleeping sickness, leishmaniasis; toxoplasmosis, i.e. infections by Plasmodium, Trypanosoma, Leishmania and Toxoplasma; or fungal infections, which are caused e.g. by Cryptococcus neoformans, Histoplasma capsulatum, Coccidioides immitis, Blastomyces dermatitidis or Candida albicans.

The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

According to the invention, an immune response may be stimulated by introducing into a subject a suitable mRNA which codes for an antigen or a fragment thereof, e.g., a disease-associated antigen.

The term "antigen" relates to an agent comprising an epitope against which an immune response is to be generated. The term "antigen" includes in particular peptides and proteins. The term "antigen" also includes agents, which become antigenic—and sensitizing—only through transformation (e.g. intermediately in the molecule or by completion with body protein). An antigen is preferably presentable by cells of the immune system such as antigen presenting cells like dendritic cells or macrophages. In addition, an antigen or a processing product thereof is preferably recognizable by a T or B cell receptor, or by an immunoglobulin molecule such as an antibody. In a preferred embodiment, the antigen is a disease-associated antigen, such as a tumor-associated antigen, a viral antigen, or a bacterial antigen.

The term "disease-associated antigen" is used in it broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "disease involving an antigen" refers to any disease which implicates an antigen, e.g. a disease which is characterized by the presence and/or expression of an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

In one embodiment, a disease-associated antigen is a tumor-associated antigen. In this embodiment, the present invention may be useful in treating cancer or cancer metastasis. Preferably, the diseased organ or tissue is characterized by diseased cells such as cancer cells expressing a disease-associated antigen and/or being characterized by association of a disease-associated antigen with their surface. Immunization with intact or substantially intact tumor-associated antigens or fragments thereof such as MHC class I and class II peptides or nucleic acids, in particular mRNA, encoding such antigen or fragment makes it possible to elicit a MHC class I and/or a class II type response and, thus, stimulate T cells such as CD8+ cytotoxic T lymphocytes which are capable of lysing cancer cells and/or CD4+ T cells. Such immunization may also elicit a humoral immune response (B cell response) resulting in the production of antibodies against the tumor-associated antigen. In one embodiment, the term "tumor-associated antigen" refers to a constituent of cancer cells which may be derived from the cytoplasm, the cell surface and the cell nucleus. In particular, it refers to those antigens which are produced, preferably in large quantity, intracellularly or as surface antigens on tumor cells. Examples for tumor-associated antigens include HER2, EGFR, VEGF, CAMPATH1-antigen, CD22, CA-125, HLA-DR, Hodgkin-lymphoma or mucin-1, but are not limited thereto.

According to the present invention, a tumor-associated antigen preferably comprises any antigen which is characteristic for tumors or cancers as well as for tumor or cancer cells with respect to type and/or expression level. In one embodiment, the term "tumor-associated antigen" relates to proteins that are under normal conditions, i.e. in a healthy subject, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably not or only rarely expressed in normal tissues or is mutated in tumor cells. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, a tumor-associated antigen is presented in the context of MHC molecules by a cancer cell in which it is expressed.

Examples for differentiation antigens which ideally fulfill the criteria for tumor-associated antigens as contemplated by the present invention as target structures in tumor immunotherapy, in particular, in tumor vaccination are the cell surface proteins of the Claudin family, such as CLDN6 and CLDN18.2. These differentiation antigens are expressed in tumors of various origins, and are particularly suited as target structures in connection with antibody-mediated cancer immunotherapy due to their selective expression (no expression in a toxicity relevant normal tissue) and localization to the plasma membrane.

Further examples for antigens that may be useful in the present invention are p53, ART-4, BAGE, beta-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

The term "immune response", as used herein, relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production. It is preferred that the immune response comprises the steps of activation of antigen presenting cells, such as dendritic cells and/or macrophages, presentation of an antigen or fragment thereof by said antigen presenting cells and activation of cytotoxic T cells due to this presentation.

The term "treat" or "treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

In particular, the term "treatment of a disease" includes curing, shortening the duration, ameliorating, slowing down or inhibiting progression or worsening of a disease or the symptoms thereof.

The term "immunotherapy" relates to a treatment preferably involving a specific immune reaction and/or immune effector function(s).

The term "immunization" or "vaccination" describes the process of treating a subject for therapeutic or prophylactic reasons.

The term "in vivo" relates to the situation in a subject.

The terms "subject" and "individual" are used interchangeably and relate to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease.

The nucleic acids such as RNA described herein, in particular when used for the treatments described herein, may be present in the form of a pharmaceutical composition or kit comprising the nucleic acid and optionally one or more pharmaceutically acceptable carriers, diluents and/or excipients.

Pharmaceutical compositions are preferably sterile and contain an effective amount of the nucleic acid.

Pharmaceutical compositions are usually provided in a uniform dosage form and may be prepared in a manner known in the art. The pharmaceutical composition may, e.g., be in the form of a solution or suspension.

The pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interfere with the action of the active component(s) of the pharmaceutical composition.

Salts which are not pharmaceutically acceptable may be used for preparing pharmaceutically acceptable salts and are included in the invention. Pharmaceutically acceptable salts of this kind comprise, in a non-limiting way, those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in the pharmaceutical composition include acetic acid in a salt, citric acid in a salt, boric acid in a salt and phosphoric acid in a salt.

Suitable preservatives for use in the pharmaceutical composition include benzalkonium chloride, chlorobutanol, paraben and thimerosal.

The term "carrier" refers to an organic or inorganic component, of a natural or non-natural (synthetic) nature, with which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are, e.g., sterile water, glucose solutions, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxy-propylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The pharmaceutical compositions described herein may be administered via any conventional route, such as by parenteral administration including by injection or infusion. Administration is preferably parenterally, e.g. intravenously, intraarterially, subcutaneously, in the lymph node, intradermally or intramuscularly.

Compositions suitable for parenteral administration usually comprise a sterile aqueous or non-aqueous preparation of the active compound, which is preferably isotonic to the blood of the recipient. Examples of compatible carriers and solvents are Ringer's solution and isotonic sodium chloride solution. In addition, usually sterile, fixed oils are used as solution or suspension medium.

The agents and compositions described herein are preferably administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on several of these parameters. In the case that a reaction in a patient is insufficient with an initial dose, higher doses (or effectively higher doses achieved by a different, more localized route of administration) may be used.

The present invention is described in detail by the following figures and examples which should be construed by way of illustration only and not by way of limitation. On the basis of the description and the examples, further embodiments are accessible to the skilled worker and are likewise within the scope of the invention.

EXAMPLES

Example 1

Generation and Purification of mRNAs

DNA encoding mouse EPO or canine EPO was ordered from and synthesized by GenScript. Coding mRNAs were produced using T7 RNA polymerase and only the 4 basic nucleotides ATP, GTP, UTP and CTP (Megascript, Ambion) from linearized plasmids encoding RNAs encoding murine erythropoietin (EPO). All mRNA contained identical 5'UTR corresponding to tobacco etch viral (TEV) leader (Gallie D R, Tanguay R L, Leathers V.: (1995) The tobacco etch viral 5' leader and poly(A) tail are functionally synergistic regulators of translation. Gene 165, 233-238) and identical 3'UTRs. Additionally, all IVT mRNA contained 100 nt-long polyA-tail interrupted by a linker (GCAUAUGACU) at nt 30 downstream from the 3' UTR. All IVT mRNA was capped using the m7G capping enzyme and 2'-O-methyltransferase (CellScript, Madison, Wis.).

Inter alia, the following murine EPO mRNAs were generated: mEPO: wild-type (wt) in which the coding sequence of EPO contained 55% GC and 125 uridine; 2) omEPO: GC-rich with 63% GC and 92 uridine; and 3) A-rich EPO with 53% GC and 80 uridine. The produced mRNAs were HPLC purified as described (Karikó, K, Muramatsu, H, Ludwig, J and Weissman, D (2011). Generating the optimal mRNA for therapy: HPLC purification eliminates immune activation and improves translation of nucleoside-modified, protein-encoding mRNA. Nucleic Acids Res 39:e142). The nucleotide composition of the non-coding region can be modified as well. For purpose of demonstrating the effect of the invention only the coding region was modified as described. All other elements of the mRNAs were kept constant as described above.

Example 2

Preparation of Lipid Nanoparticles (LNP) Entrapping mRNA

LNPs were prepared by using a microfluidic mixing device, the NanoAssemblr Benchtop Instrument (Precision NanoSystems, Vancouver, BC). One volume of lipids mixture in ethanol (DLin-KC2-DMA (DLin-KC2-DMA was synthetized according to Semple, S C, Akinc, A, Chen, J, Sandhu, A P, Mui, B L, Cho, C K et al. (2010) and Rational design of cationic lipids for siRNA delivery. Nat Biotechnol 28: 172-176.), Cholesterol (Sigma Aldrich, Taufkirchen Germany), DSPC (1,2-Distearoyl-sn-glycero-3-phosphocholine, Corden Pharm, Liestal Switzerland), mPEG2000-CeramideC16 (Avanti Polar Lipids, Alabaster, Ala., USA) at an appropriate molar ratio) and 3 volumes of RNA in citrate buffer 100 mM, pH 5.4 (17:1 w/w lipid/RNA) were mixed through the microfluidic cartridge at a combined flow rate of 12 mL/min (3 mL/min for ethanol and 9 mL/min for aqueous buffer). The resultant phase was directly mixed with 2 volumes of citrate buffer 100 mM, pH 5.4. The mixture was then dialyzed against phosphate buffered saline (PBS) for 2.5 h to remove ethanol in a Slide-A-Lyser dialysis cassette (10K MWCO, ThermoFisher Scientific). The particles were then re-concentrated by ultrafiltration using Amicon Ultra Centrifugal filters (30 kDa NMWL, Merck Millipore) to a total RNA concentration of about 0.3 to 0.5 mg/mL. siRNA encapsulation efficiency was determined by the Quant-iT RiboGreen RNA assay (Life Technologies). Briefly, the encapsulation efficiency was determined using the RNA binding dye RiboGreen by comparing fluorescence between LNPs in the presence and absence of 0.5% Triton X-100. In the absence of detergent, fluorescence can be measured from accessible free RNA only, whereas in the presence of detergent, fluorescence is measured from the total RNA amount.

Example 3

Preparation of TransIT-Complexed mRNA mRNA generated according to example 1 was complexed to TransIT-mRNA (Mirus Bio, Madison, Wis.) according to the manufacturer. In a regular polypropylene tube, first Dulbecco's modified Eagle's medium (DMEM) was measured then 1 µg mRNA was added quickly, followed by 1.1 µl TransIT-mRNA reagent and 0.7 µl Boost reagent to obtain the complex in a final volume of 100 µl DMEM. The components were combined and vortexed for 20 second, then let stand for 2 min and injected immediately. For complexing different amounts of mRNA the volumes of the reagents and the final volume were scaled proportionally.

Example 4

Preparation of Liposomal mRNA Formulation

Liposomes were manufactured by a modification of the so-called ethanol injection technique, where an ethanolic solution of the lipids is injected under stirring into an aqueous phase. As lipids, the synthetic cationic lipid DOTMA and the phospholipid DOPE in a molar ratio of 2:1 were used. A manufacturing protocol resulting in liposomes in the size range of about 400 nm, in order to obtain the appropriate size of the RNA-lipoplexes was used. Briefly, an ethanol solution of the lipids was prepared, sterile filtrated, and injected into water for injection (WFI) under stirring to obtain a lipid concentration in the aqueous phase of about 6 to 10 mM. Thus a liposome raw dispersion with pre-defined size was obtained. Subsequently the liposome raw dispersion was filtrated in order to reduce the amount of larger aggregates. Subsequently, the lipid content of the liposome dispersion was determined, and, depending on the result, the liposomes were diluted with WFI to a final concentration of about 4 mM. The liposomes were filled in depyrogenated and sterilized 10 mL glass vials which were closed with sterilized stoppers and flip-off crimping caps.

The mRNA was prepared to obtain liposomal 20 µg mRNA in a 200 µl final volume. First, the RNA was diluted to obtain 1 µg RNA/µl of HEPES/EDTA in a final concentration of 10 mM HEPES/0.1 mM EDTA. An aliquot of 20 µl of RNA was measured into an eppendorf tube then 146 µl water and 20 µl of 1.5 M NaCl were added and mixed well. The RNA solution was incubated at room temperature for 2 minutes, then 14 µl of liposomal solution was added, vortexed, then incubated at room temperature for 10 min. Finally the liposomal mRNA was used for the experiments or injected.

Example 5

Administration/Injection of Formulated mRNAs

Formulated mRNAs according to examples 2 to 4 were administered in vitro to human dendritic cells or in vivo to BALB/c mice as follows:

Human dendritic cells were transfected with 0.1 µg of TransIT-complexed mRNA according to example 3. The purification of DCs from PBMCs used the method originally described by Sallusto and Lanzavecchia (Sallusto, F., and A. Lanzavecchia. 1994. Efficient presentation of soluble antigen by cultured human dendritic cells is maintained by granulocyte/macrophage colony-stimulating factor plus interleukin 4 and downregulated by tumor necrosis factor a. J. Exp. Med. 179:1109) with minor modification. Briefly, monocytes were purified from PBMC by Ficoll density gradient centrifugation. Human CD14+ cells were selected by positive selection using CD14 MicroBeads (Miltenyi Biotec). To generate immature DC, purified monocytes were cultured for 4 days in RPMI 1640 supplemented with glutamine (2 mM), HEPES (15 mM), 1% NHS (Sigma), GM-CSF (50 ng/ml) and IL-4 (100 ng/ml). Cells were seeded into 96-well plate at 1×105 cells/200 µl/well density in culture medium supplemented with 10% FCS. Cells were transfected by adding 17 µl of TransIT-complexed 0.1 µg mRNA/well. The complex was generated as described in Example 3. Cells were cultured overnight and the medium was harvested at 24 h posttransfection. Murine EPO level was measured by ELISA (Erythropoietin DuoSet ELISA Development kit, R&D) and murine IFN was measured also by ELISA (eBioscience, Platinum ELISA)

20 µg of liposomal-complexed mRNAs according to example 4 were injected intravenously, by retro-orbital route to 6-weeks old BALB/c mice, 5 animals/group. At 6 h following injection animals were bleed and EDTA was used to inhibit coagulation of the drawn blood. Plasma was separated by centrifugation and collected. Murine EPO level was measured by ELISA (Erythropoietin DuoSet ELISA Development kit, R&D) and murine IFN was measured also by ELISA (eBioscience, Platinum ELISA)

10 µg of LNP-formulated mRNAs according to example 2 were injected intravenously, by retro-orbital route to 6-weeks old BALB/c mice, 5 animals/group. At 6 h following injection, animals were bleed and EDTA was used to inhibit coagulation of the drawn blood. Plasma was separated by centrifugation and collected. Murine EPO level was measured by ELISA (Erythropoietin DuoSet ELISA Development kit, R&D) and murine IFN was measured also by ELISA (eBioscience, Platinum ELISA). Results are shown in FIG. 2.

Sequences

Amino Acid Sequence:

All used/codon-optimized murine EPO nucleic acid sequences encode the same murine EPO protein with the following amino acid sequence:

MGVPERPTLLLLLSLLLIPLGLPVLCAPPRLICDSRVLERYILEAKEAEN

VTMGCAEGPRLSENITVPDTKVNFYAWKRMEVEEQAIEVWQGLSLLSEAI

LQAQALLANSSQPPETLQLHIDKAISGLRSLTSLLRVLGAQKELMSPPDT

TPPAPLRTLTVDTFCKLFRVYANFLRGKLKLYTGEVCRRGDR.

Nucleic Acid Sequences:

1) Original murine EPO coding sequences, also called murine EPO (mEPO) or wild-type EPO (wt EPO):

ATGGGGGTGCCCGAACGTCCCACCCTGCTGCTTTTACTCTCCTTGCTACT

GATTCCTCTGGGCCTCCCAGTCCTCTGTGCTCCCCCACGCCTCATCTGCG

ACAGTCGAGTTCTGGAGAGGTACATCTTAGAGGCCAAGGAGGCAGAAAAT

GTCACGATGGGTTGTGCAGAAGGTCCCAGACTGAGTGAAAATATTACAGT

CCCAGATACCAAAGTCAACTTCTATGCTTGGAAAAGAATGGAGGTGGAAG

AACAGGCCATAGAAGTTTGGCAAGGCCTGTCCCTGCTCTCAGAAGCCATC

CTGCAGGCCCAGGCCCTGCTAGCCAATTCCTCCCAGCCACCAGAGACCCT

TCAGCTTCATATAGACAAAGCCATCAGTGGTCTACGTAGCCTCACTTCAC

TGCTTCGGGTACTGGGAGCTCAGAAGGAATTGATGTCGCCTCCAGATACC

ACCCCACCTGCTCCACTCCGAACACTCACAGTGGATACTTTCTGCAAGCT

CTTCCGGGTCTACGCCAACTTCCTCCGGGGGAAACTGAAGCTGTACACGG

GAGAGGTCTGCAGGAGAGGGGACAGGTGA

2) GC-rich murine EPO coding sequence, also called optimized murine EPO (omEPO). This sequence was codon-optimized by GeneArt AG, Regensburg:

ATGGGCGTCCCCGAAAGGCCTACCCTGCTGCTGCTCCTGTCTCTGCTCCT

GATCCCCCTGGGACTGCCCGTGCTGTGCGCCCCTCCCAGGCTGATCTGCG

ACAGCAGGGTGCTGGAAAGATACATCCTGGAAGCCAAAGAGGCCGAGAAC

GTCACAATGGGCTGCGCCGAGGGCCCCAGACTGAGCGAGAACATCACCGT

GCCCGACACCAAGGTCAACTTCTACGCCTGGAAGAGGATGGAAGTGGAGG

AACAGGCCATCGAGGTCTGGCAGGGACTGTCTCTGCTGTCCGAGGCCATC

CTGCAGGCCCAGGCTCTGCTGGCCAATTCTAGCCAGCCCCCCGAGACACT

3) A-Rich Murine EPO Coding Sequence:

```
GCAGCTGCACATCGACAAGGCCATCAGCGGCCTGAGAAGCCTGACCAGCC
TGCTGAGGGTGCTGGGAGCCCAGAAAGAGCTGATGAGCCCCCCTGACACC
ACCCCCCCTGCCCCCCTGAGGACCCTGACCGTGGACACCTTCTGCAAGCT
GTTCAGGGTGTACGCCAACTTCCTGAGGGGCAAGCTGAAGCTGTACACCG
GCGAGGTCTGCAGACGGGGCGACAGATGA
```

3) A-Rich Murine EPO Coding Sequence:

```
ATGGGAGTGCCAGAAAGACCAACCCTGCTGCTGCTGCTCAGCCTGCTACT
GATCCCACTGGGACTCCCAGTCCTCTGCGCACCACCAAGACTCATCTGCG
ACAGCAGAGTGCTGGAAAGATACATCCTAGAAGCAAAAGAAGCAGAAAAC
GTCACGATGGGATGCGCAGAAGGACCAAGACTGAGCGAAAACATCACAGT
CCCAGACACCAAAGTCAACTTCTACGCATGGAAAAGAATGGAAGTGGAAG
AACAGGCAATAGAAGTGTGGCAAGGACTGAGCCTGCTCAGCGAAGCAATC
CTGCAGGCACAGGCACTGCTAGCAAACAGCAGCCAGCCACCAGAAACCCT
GCAGCTGCACATAGACAAAGCAATCAGCGGACTAAGAAGCCTCACCAGCC
TGCTGAGAGTACTGGGAGCACAGAAAGAACTGATGAGCCCACCAGACACC
ACCCCACCAGCACCACTCAGAACACTCACAGTGGACACTTTCTGCAAACT
CTTCAGAGTCTACGCAAACTTCCTCAGAGGAAAACTGAAACTGTACACGG
GAGAAGTCTGCAGAAGAGGGGACAGATGA
```

4) Super optimized murine EPO (somEPO), optimized by Entelechon using Entelechon's proprietary algorithm and codon-optimized human EPO (Kim, C H, Oh, Y and Lee, T H (1997). Codon optimization for high-level expression of human erythropoietin (EPO) in mammalian cells. Gene 199: 293-301). This sequence was used previously, e.g. described in Kariko, K. et al. Kariko K, Muramatsu H, Keller J M, Weissman D (2012) Increased erythropoiesis in mice injected with submicrogram quantities of pseudouridine-containing mRNA encoding erythropoietin. Mol Ther 20:948-953.

```
ATGGGAGTTCCTGAAAGACCAACTCTGTTGCTCTTGCTGTCTTTGCTGCT
GATTCCTCTGGGTCTTCCGGTGCTTTGCGCACCTCCCAGGCTTATCTGCG
ATAGCAGGGTGCTTGAGAGGTACATCCTGGAAGCTAAAGAAGCCGAAAAC
GTGACCATGGGCTGCGCCGAGGGCCCTAGGCTCAGTGAAAACATTACTGT
TCCCGATACGAAAGTCAATTTCTACGCCTGGAAGCGGATGGAAGTGGAGG
AACAGGCCATAGAGGTGTGGCAAGGTCTGTCTCTCCTGAGCGAGGCAATC
CTTCAAGCCCAGGCTCTGCTGGCCAATTCAAGCCAGCCACCCGAGACCCT
CCAGCTGCACATTGACAAGGCTATCAGCGGTCTGAGATCCCTGACGTCCC
TGTTGCGAGTCCTGGGCGCTCAGAAGGAGCTGATGAGTCCACCCGATACC
ACACCTCCAGCACCGCTCCGCACACTCACTGTGGACACCTTTTGTAAACT
GTTCAGAGTCTACGCCAACTTTCTGCGAGGCAAGCTGAAGCTCTATACAG
GAGAGGTGTGTAGGAGAGGAGACCGGTGA
```

5) GC-maximized murine EPO (as described in Thess, A., Grund, S., Mui, B. L., Hope, M. J., Baumhof, P., Fotin-Mleczek, M., and Schlake, T. (2015) Sequence-engineered mRNA without chemical nucleoside modifications enables an effective protein therapy in large animals (Molecular Therapy 23, 1457-1465):

```
ATGGGCGTGCCCGAGCGGCCGACCCTGCTCCTGCTGCTCAGCCTGCTGCT
CATCCCCCTGGGGCTGCCCGTCCTCTGCGCCCCCCCGCGCCTGATCTGCG
ACTCCCGGGTGCTGGAGCGCTACATCCTCGAGGCCAAGGAGGCGGAGAAC
GTGACCATGGGCTGCGCCGAGGGGCCCCGGCTGAGCGAGAACATCACGGT
CCCCGACACCAAGGTGAACTTCTACGCCTGGAAGCGCATGGAGGTGGAGG
AGCAGGCCATCGAGGTCTGGCAGGGCCTGTCCCTCCTGAGCGAGGCCATC
CTGCAGGCGCAGGCCCTCCTGGCCAACTCCAGCCAGCCCCCGGAGACACT
GCAGCTCCACATCGACAAGGCCATCTCCGGGCTGCGGAGCCTGACCTCCC
TCCTGCGCGTGCTGGGCGCGCAGAAGGAGCTCATGAGCCCGCCCGACACG
ACCCCCCCGGCCCCGCTGCGGACCCTGACCGTGGACACGTTCTGCAAGCT
CTTCCGCGTCTACGCCAACTTCCTGCGGGGCAAGCTGAAGCTCTACACCG
GGGAGGTGTGCCGCCGGGCGACCGCTGA
```

6) Amino Acid Sequence:

All used/codon-optimized canine EPO (*Canis lupus familiaris*) nucleic acid sequences encode the same canine EPO protein with the following amino acid sequence (Swiss-Prot No. J9NYY7):

```
MCEPAPPKPTQSAWHSFPECPALLLLLSLLLLPLGLPVLGAPPRLICDSR
VLERYILEAREAENVTMGCAQGCSFSENITVPDTKVNFYTWKRMDVGQQA
LEVWQGLALLSEAILRGQALLANASQPSETPQLHVDKAVSSLRSLTSLLR
ALGAQKEAMSLPEEASPAPLRTFTVDTLCKLFRIYSNFLRGKLTLYTGEA
CRRGDR
```

Nucleic Acid Sequences:

7) Original canine EPO coding sequences, also called canine EPO (cEPO) or wild-type EPO (wt EPO):

```
ATGTGCGAACCCGCCCCACCTAAGCCCACTCAGTCTGCTTGGCACAGTTT
CCCCGAATGTCCAGCTCTCCTGCTGCTGCTCTCCCTGCTGCTCCTGCCCC
TCGGGCTGCCTGTGCTGGGCGCTCCTCCAAGACTCATCTGCGACAGCAGG
GTGCTGGAGCGGTACATCCTGGAGGCTAGAGAAGCCGAGAATGTCACCAT
GGGGTGTGCTCAGGGATGCTCCTTCAGCGAGAACATCACCGTGCCCGACA
CTAAGGTGAACTTCTATACATGGAAGCGGATGGATGTGGGACAGCAGGCC
CTCGAAGTGTGGCAGGGCCTCGCTCTGCTGTCTGAAGCCATCCTGAGGGG
ACAGGCCCTCCTGGCTAATGCCAGCCAGCCTTCAGAGACCCCCCAGCTGC
ACGTGGACAAAGCCGTGTCAAGCCTGAGATCCCTCACAAGCCTCCTGAGG
GCTCTGGGCGCTCAGAAGGAAGCCATGTCTCTGCCAGAGGAAGCCAGCCC
TGCCCCACTCAGGACCTTCACTGTCGATACCCTGTGCAAGCTGTTCAGGA
TCTATTCCAACTTTCTGAGGGGCAAACTGACACTCTATACTGGGGAGGCT
TGTAGGCGGGGAGACCGATGA
```

8) A-Rich Canine EPO Coding Sequence:

ATGTGCGAACCAGCACCACCTAAACCAACACAGAGCGCATGGCACAGCTT

CCCAGAATGCCCAGCACTGCTGCTGCTGCTCAGCCTGCTACTGCTGCCAC

TGGGACTCCCAGTCCTCGGAGCACCACCAAGACTCATCTGCGACAGCAGA

GTGCTGGAAAGATACATCCTAGAAGCAAGAGAAGCAGAAAACGTCACGAT

GGGATGCGCACAAGGATGCAGCTTCAGCGAAAACATCACAGTCCCAGACA

CCAAAGTCAACTTCTACACATGGAAAAGAATGGACGTGGGACAGCAGGCA

CTGGAAGTGTGGCAAGGACTGGCACTGCTCAGCGAAGCAATCCTGAGAGG

ACAGGCACTGCTAGCAAACGCAAGCCAGCCAAGCGAAACCCCACAGCTGC

ACGTAGACAAAGCAGTGAGCAGCCTAAGAAGCCTCACCAGCCTGCTGAGA

GCACTGGGAGCACAGAAAGAAGCCATGAGCCTGCCAGAAGAAGCCAGCCC

AGCACCACTCAGAACATTCACAGTGGACACCCTGTGCAAACTGTTCAGAA

TATACAGCAACTTCCTCAGAGGAAAACTGACACTGTACACGGGAGAAGCT

TGCAGAGGAGGAGACAGATGA

The invention claimed is:

1. A method of decreasing immunogenicity of RNA encoding at least one peptide or protein and comprising a first nucleotide sequence, said method comprising substituting uridine (U) nucleotide residues of the first nucleotide sequence with nucleotide residues selected from the group consisting of adenosine (A), guanosine (G), and cytidine (C) nucleotide residues, thereby forming an A-rich second nucleotide sequence encoding the same peptide or protein as the first nucleotide sequence; wherein the second nucleotide sequence has a higher A content and a lower U content compared to the first nucleotide sequence, thereby rendering RNA comprising the second nucleotide sequence less immunogenic than RNA comprising the first nucleotide sequence.

2. The method of claim 1, wherein the peptide or protein encoded by the first and second nucleotide sequences is pharmaceutically active or antigenic.

3. The method of claim 1, wherein the U content in the RNA comprising the second nucleotide sequence is at least 10% lower, at least 20% lower, or at least 30% lower than the U content of to the RNA comprising the first nucleotide sequence.

4. The method of claim 1, wherein the U content of the second nucleotide sequence is lower in one or more of the 5' untranslated region, the coding region and the 3' untranslated region thereof compared to the U content of corresponding regions of the first nucleotide sequence.

5. The method of claim 1, wherein the U content of the second nucleotide sequence is lower in the coding region thereof, compared to U content of the coding region of the first nucleotide sequence.

6. The method of claim 1, wherein the substituting comprises substituting U nucleotide residues with A nucleotide residues.

7. The method of claim 1, wherein the step of substituting U nucleotide residues comprises altering codons in the coding region of the first nucleotide sequence that comprise at least one U nucleotide residue resulting in codons that encode the same amino acids but comprise fewer U nucleotide residues or no U nucleotide residues.

* * * * *

UNITED STATES PATENT AND TRADEMARK OFFICE
CERTIFICATE OF CORRECTION

| | |
|---|---|
| PATENT NO. | : 10,808,242 B2 |
| APPLICATION NO. | : 15/755309 |
| DATED | : October 20, 2020 |
| INVENTOR(S) | : Katalin Kariko and Ugur Sahin |

It is certified that error appears in the above-identified patent and that said Letters Patent is hereby corrected as shown below:

On the Title Page

Delete the following:
"Related U.S. Application Data
(63) Continuation-in-part of application No. PCT/EP2015/069760, filed on Aug. 28, 2015".

Before (51) insert the following:
--Foreign Application Priority Data
(30) Aug. 28, 2015 (EP) .......... PCT/EP2015/069760--.

In the Specification

Column 1, Lines 8-10, delete ", which is a continuation-in-part of International Application No. PCT/EP2015/069760, filed on Aug. 28, 2015, each of".

Signed and Sealed this
Seventh Day of May, 2024

Katherine Kelly Vidal
*Director of the United States Patent and Trademark Office*

SEQUENCE LISTING

<160> NUMBER OF SEQ ID NOS: 15

<210> SEQ ID NO 1
<211> LENGTH: 192
<212> TYPE: PRT
<213> ORGANISM: Mus musculus

<400> SEQUENCE: 1

Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Arg Leu Ile
            20                  25                  30

Cys Asp Ser Arg Val Leu Glu Arg Tyr Ile Leu Glu Ala Lys Glu Ala
            35                  40                  45

Glu Asn Val Thr Met Gly Cys Ala Glu Gly Pro Arg Leu Ser Glu Asn
            50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
                85                  90                  95

Ser Glu Ala Ile Leu Gln Ala Gln Ala Leu Leu Ala Asn Ser Ser Gln
            100                 105                 110

Pro Pro Glu Thr Leu Gln Leu His Ile Asp Lys Ala Ile Ser Gly Leu
            115                 120                 125

Arg Ser Leu Thr Ser Leu Leu Arg Val Leu Gly Ala Gln Lys Glu Leu
    130                 135                 140

Met Ser Pro Pro Asp Thr Thr Pro Ala Pro Leu Arg Thr Leu Thr
145                 150                 155                 160

Val Asp Thr Phe Cys Lys Leu Phe Arg Val Tyr Ala Asn Phe Leu Arg
                165                 170                 175

Gly Lys Leu Lys Leu Tyr Thr Gly Glu Val Cys Arg Arg Gly Asp Arg
            180                 185                 190

<210> SEQ ID NO 2
<211> LENGTH: 579
<212> TYPE: DNA
<213> ORGANISM: Mus musculus

<400> SEQUENCE: 2
atgggggtgc cgaacgtcc caccctgctg cttttactct ccttgctact gattcctctg      60
ggcctcccag tcctctgtgc tccccacgc ctcatctgcg acagtcgagt tctggagagg     120
tacatcttag aggccaagga ggcagaaaat gtcacgatgg gttgtgcaga aggtcccaga     180
ctgagtgaaa atattacagt cccagatacc aaagtcaact tctatgcttg gaaaagaatg     240

-continued

| | |
|---|---|
| gaggtggaag aacaggccat agaagtttgg caaggcctgt ccctgctctc agaagccatc | 300 |
| ctgcaggccc aggccctgct agccaattcc tcccagccac cagagaccct tcagcttcat | 360 |
| atagacaaag ccatcagtgg tctacgtagc ctcacttcac tgcttcgggt actgggagct | 420 |
| cagaaggaat tgatgtcgcc tccagatacc accccacctg ctccactccg aacactcaca | 480 |
| gtggatactt tctgcaagct cttccgggtc tacgccaact tcctccgggg gaaactgaag | 540 |
| ctgtacacgg agaggtctg caggagaggg gacaggtga | 579 |

<210> SEQ ID NO 3
<211> LENGTH: 579
<212> TYPE: DNA
<213> ORGANISM: Artificial Sequence
<220> FEATURE:
<223> OTHER INFORMATION: GC-rich sequence

<400> SEQUENCE: 3

| | |
|---|---|
| atgggcgtcc ccgaaaggcc taccctgctg ctgctcctgt ctctgctcct gatcccctg | 60 |
| ggactgcccg tgctgtgcgc ccctcccagg ctgatctgcg acagcagggt gctggaaaga | 120 |
| tacatcctgg aagccaaaga ggccgagaac gtcacaatgg gctgcgccga gggccccaga | 180 |
| ctgagcgaga acatcaccgt gcccgacacc aaggtcaact tctacgcctg gaagaggatg | 240 |
| gaagtggagg aacaggccat cgaggtctgg cagggactgt ctctgctgtc cgaggccatc | 300 |
| ctgcaggccc aggctctgct ggccaattct agccagcccc ccgagacact gcagctgcac | 360 |
| atcgacaagg ccatcagcgg cctgagaagc ctgaccagcc tgctgagggt gctgggagcc | 420 |
| cagaaagagc tgatgagccc ccctgacacc acccccctg ccccctgag gaccctgacc | 480 |
| gtggacacct tctgcaagct gttcagggtg tacgccaact tcctgagggg caagctgaag | 540 |
| ctgtacaccg gcgaggtctg cagacgggc gacagatga | 579 |

<210> SEQ ID NO 4
<211> LENGTH: 579
<212> TYPE: DNA
<213> ORGANISM: Artificial Sequence
<220> FEATURE:
<223> OTHER INFORMATION: A-rich sequence

<400> SEQUENCE: 4

| | |
|---|---|
| atgggagtgc cagaaagacc aaccctgctg ctgctgctca gcctgctact gatcccactg | 60 |
| ggactcccag tcctctgcgc accaccaaga ctcatctgcg acagcagagt gctggaaaga | 120 |
| tacatcctag aagcaaaaga agcagaaaac gtcacgatgg gatgcgcaga aggaccaaga | 180 |
| ctgagcgaaa acatcacagt cccagacacc aaagtcaact tctacgcatg gaaaagaatg | 240 |
| gaagtggaag aacaggcaat agaagtgtgg caaggactga gcctgctcag cgaagcaatc | 300 |
| ctgcaggcac aggcactgct agcaaacagc agccagccac cagaaaccct gcagctgcac | 360 |
| atagacaaag caatcagcgg actaagaagc ctcaccagcc tgctgagagt actgggagca | 420 |
| cagaaagaac tgatgagccc accagacacc accccaccag caccactcag aacactcaca | 480 |
| gtggacactt tctgcaaaact cttcagagtc tacgcaaact tcctcagagg aaaactgaaa | 540 |
| ctgtacacgg agaagtctg cagaagaggg gacagatga | 579 |

<210> SEQ ID NO 5
<211> LENGTH: 579
<212> TYPE: DNA
<213> ORGANISM: Artificial Sequence
<220> FEATURE:
<223> OTHER INFORMATION: Super optimized sequence

<400> SEQUENCE: 5

```
atgggagttc ctgaaagacc aactctgttg ctcttgctgt ctttgctgct gattcctctg      60
ggtcttccgg tgctttgcgc acctcccagg cttatctgcg atagcagggt gcttgagagg     120
tacatcctgg aagctaaaga agccgaaaac gtgaccatgg gctgcgccga gggccctagg     180
ctcagtgaaa acattactgt tcccgatacg aaagtcaatt tctacgcctg aagcggatg      240
gaagtggagg aacaggccat agaggtgtgg caaggtctgt ctctcctgag cgaggcaatc     300
cttcaagccc aggctctgct ggccaattca agccagccac ccgagaccct ccagctgcac     360
attgacaagg ctatcagcgg tctgagatcc ctgacgtccc tgttgcgagt cctgggcgct     420
cagaaggagc tgatgagtcc acccgatacc acacctccag caccgctccg cacactcact     480
gtggacacct tttgtaaact gttcagagtc tacgccaact ttctgcgagg caagctgaag     540
ctctatacag gagaggtgtg taggagagga gaccggtga                            579
```

<210> SEQ ID NO 6
<211> LENGTH: 579
<212> TYPE: DNA
<213> ORGANISM: Artificial Sequence
<220> FEATURE:
<223> OTHER INFORMATION: GC-maximized sequence

<400> SEQUENCE: 6

```
atgggcgtgc ccgagcggcc gaccctgctc ctgctgctca gcctgctgct catccccctg      60
gggctgcccg tcctctgcgc ccccccgcgc ctgatctgcg actcccgggt gctggagcgc     120
tacatcctcg aggccaagga ggcggagaac gtgaccatgg gctgcgccga ggggccccgg     180
ctgagcgaga acatcacggt ccccgacacc aaggtgaact tctacgcctg aagcgcatg      240
gaggtggagg agcaggccat cgaggtctgg cagggcctgt ccctcctgag cgaggccatc     300
ctgcaggcgc aggccctcct ggccaactcc agccagcccc ggagacact gcagctccac     360
atcgacaagg ccatctccgg gctgcgggagc ctgacctccc tcctgcgcgt gctgggcgcg     420
cagaaggagc tcatgagccc gcccgacacg accccccgg ccccgctgcg gaccctgacc     480
gtggacacgt tctgcaagct cttccgcgtc tacgccaact tcctgcgggg caagctgaag     540
ctctacaccg gggaggtgtg ccgccggggc gaccgctga                            579
```

<210> SEQ ID NO 7
<211> LENGTH: 579
<212> TYPE: RNA
<213> ORGANISM: Mus musculus

<400> SEQUENCE: 7

```
auggggguge ccgaacgucc cacccugcug cuuuuacucu ccugcuacu gauuccucug      60
ggccucccag uccucugugc uccccacgc cucaucugcg acagucgagu ucuggagagg     120
uacaucuuag aggccaagga ggcagaaaau gucacgaugg guugugcaga aggucccaga     180
cugagugaaa auauuacagu cccagauacc aaagucaacu ucuaugcuug aaaagaaug      240
gaggggaag aacaggccau agaaguuugg caaggccugu cccugcucuc agaagccauc     300
cugcaggccc aggcccugcu agccaauucc ucccagccac cagagacccu ucagcuucau     360
auagacaaag ccaucagugg ucuacguagc cucacuuuac ugcuucgggu acuggagcu      420
cagaaggaau ugaugucgcc uccagauacc accccaccug cuccacuccg aacacucaca     480
guggauacuu ucugcaagcu cuuccggguc uacgccaacu uccuccgggg gaaacugaag     540
cuguacacgg gagaggucug caggagaggg gacagguga                            579
```

-continued

```
<210> SEQ ID NO 8
<211> LENGTH: 579
<212> TYPE: RNA
<213> ORGANISM: Artificial Sequence
<220> FEATURE:
<223> OTHER INFORMATION: GC-rich sequence

<400> SEQUENCE: 8
augggcgucc ccgaaaggcc uacccugcug cugcuccugu cucugcuccu gauccccug      60 ggacugccg ugcugugcgc cccucccagg cugaucugcg acagcagggu gcuggaaaga    120
uacauccugg aagccaaaga ggccgagaac gucacaaugg gcugcgccga gggccccaga   180
cugagcgaga acaucaccgu gcccgacacc aagucaacu ucuacgccug gaagaggaug    240
gaaguggagg aacaggccau cgaggucugg cagggacugu cucugcuguc cgaggccauc   300
cugcaggccc aggcucugcu ggccaauucu agccagcccc ccgagacacu gcagcugcac   360
aucgacaagg ccaucagcgg ccugagaagc cugaccagcc ugcugagggu gcuggagcc    420 cagaaagagc ugaugagccc cccugacacc accccccug ccccccugag gacccugacc    480
guggacaccu ucugcaagcu guucaggug uacgccaacu uccugagggg caagcugaag    540
cuguacaccg gcgaggucug cagacggggc gacagauga                          579

<210> SEQ ID NO 9
<211> LENGTH: 579
<212> TYPE: RNA
<213> ORGANISM: Artificial Sequence
<220> FEATURE:
<223> OTHER INFORMATION: A-rich sequence

<400> SEQUENCE: 9
augggagugc cagaaagacc aacccugcug cugcugcuca gccugcuacu gaucccacug     60
ggacucccag uccucugcgc accaccaaga cucaucugcg acagcagagu gcuggaaaga   120
uacauccuag aagcaaaaga agcagaaaac gucacgaugg gaugcgcaga aggaccaaga   180
cugagcgaaa acaucacagu cccagacacc aaagucaacu ucuacgcaug gaaagaaug    240 gaaguggaag aacaggcaau agaagugugg caaggacuga gccugcucag cgaagcaauc   300
cugcaggcac aggcacugcu agcaaacagc agccagccac cagaaacccu gcagcugcac   360
auagacaaag caaucagcgg acuaagaagc cucaccagcc ugcugagagu acugggagca   420
cagaaagaac ugaugagccc accagacacc accccaccag caccacucag aacacucaca   480
guggacacuu ucugcaaacu cuucagaguc uacgcaaacu uccucagagg aaaacugaaa   540
cuguacacgg gagaagucug cagaagaggg gacagauga                          579

<210> SEQ ID NO 10
<211> LENGTH: 10
<212> TYPE: RNA
<213> ORGANISM: Artificial Sequence
<220> FEATURE:
<223> OTHER INFORMATION: Linker

<400> SEQUENCE: 10
gcauaugacu                                                           10

<210> SEQ ID NO 11
<211> LENGTH: 206
<212> TYPE: PRT
<213> ORGANISM: Canis familiaris
```

<400> SEQUENCE: 11

```
Met Cys Glu Pro Ala Pro Pro Lys Pro Thr Gln Ser Ala Trp His Ser
1               5                   10                  15

Phe Pro Glu Cys Pro Ala Leu Leu Leu Leu Ser Leu Leu Leu Leu
            20                  25                  30

Pro Leu Gly Leu Pro Val Leu Gly Ala Pro Pro Arg Leu Ile Cys Asp
        35                  40                  45

Ser Arg Val Leu Glu Arg Tyr Ile Leu Glu Ala Arg Glu Ala Glu Asn
    50                  55                  60

Val Thr Met Gly Cys Ala Gln Gly Cys Ser Phe Ser Glu Asn Ile Thr
65                  70                  75                  80

Val Pro Asp Thr Lys Val Asn Phe Tyr Thr Trp Lys Arg Met Asp Val
                85                  90                  95

Gly Gln Gln Ala Leu Glu Val Trp Gln Gly Leu Ala Leu Leu Ser Glu
            100                 105                 110

Ala Ile Leu Arg Gly Gln Ala Leu Leu Ala Asn Ala Ser Gln Pro Ser
        115                 120                 125

Glu Thr Pro Gln Leu His Val Asp Lys Ala Val Ser Ser Leu Arg Ser
130                 135                 140

Leu Thr Ser Leu Leu Arg Ala Leu Gly Ala Gln Lys Glu Ala Met Ser
145                 150                 155                 160

Leu Pro Glu Glu Ala Ser Pro Ala Pro Leu Arg Thr Phe Thr Val Asp
                165                 170                 175

Thr Leu Cys Lys Leu Phe Arg Ile Tyr Ser Asn Phe Leu Arg Gly Lys
            180                 185                 190

Leu Thr Leu Tyr Thr Gly Glu Ala Cys Arg Arg Gly Asp Arg
        195                 200                 205
```

<210> SEQ ID NO 12
<211> LENGTH: 621
<212> TYPE: DNA
<213> ORGANISM: Canis familiaris

<400> SEQUENCE: 12

```
atgtgcgaac cgcccccacc taagcccact cagtctgctt ggcacagttt ccccgaatgt    60
ccagctctcc tgctgctgct ctccctgctg ctcctgcccc tcgggctgcc tgtgctgggc   120
gctcctccaa gactcatctg cgacagcagg gtgctggagc ggtacatcct ggaggctaga   180
gaagccgaga atgtcaccat ggggtgtgct cagggatgct ccttcagcga aaacatcacc   240
gtgcccgaca ctaaggtgaa cttctataca tggaagcgga tggatgtggg acagcaggcc   300
ctcgaagtgt ggcagggcct cgctctgctg tctgaagcca tcctgagggg acaggccctc   360
ctggctaatg ccagccagcc ttcagagacc ccccagctgc acgtggacaa agccgtgtca   420
agcctgagat ccctcacaag cctcctgagg gctctgggcg ctcagaagga agccatgtct   480
ctgccagagg aagccagccc tgccccactc aggaccttca ctgtcgatac cctgtgcaag   540
ctgttcagga tctattccaa ctttctgagg ggcaaactga cactctatac tggggaggct   600
tgtaggcggg gagaccgatg a                                             621
```

<210> SEQ ID NO 13
<211> LENGTH: 621
<212> TYPE: DNA
<213> ORGANISM: Artificial Sequence
<220> FEATURE:
<223> OTHER INFORMATION: A-rich sequence

<400> SEQUENCE: 13

```
atgtgcgaac cagcaccacc taaaccaaca cagagcgcat ggcacagctt cccagaatgc    60
ccagcactgc tgctgctgct cagcctgcta ctgctgccac tgggactccc agtcctcgga   120
gcaccaccaa gactcatctg cgacagcaga gtgctggaaa gatacatcct agaagcaaga   180
gaagcagaaa acgtcacgat gggatgcgca caaggatgca gcttcagcga aaacatcaca   240
gtcccagaca ccaaagtcaa cttctacaca tggaaaagaa tggacgtggg acagcaggca   300
ctggaagtgt ggcaaggact ggcactgctc agcgaagcaa tcctgagagg acaggcactg   360
ctagcaaacg caagccagcc aagcgaaacc ccacagctgc acgtagacaa agcagtgagc   420
agcctaagaa gcctcaccag cctgctgaga gcactgggag cacagaaaga agccatgagc   480
ctgccagaag aagccagccc agcaccactc agaacattca cagtggacac cctgtgcaaa   540
ctgttcagaa tatacagcaa cttcctcaga ggaaaactga cactgtacac gggagaagct   600
tgcagaggag gagacagatg a                                             621
```

<210> SEQ ID NO 14
<211> LENGTH: 621
<212> TYPE: RNA
<213> ORGANISM: Canis familiaris

<400> SEQUENCE: 14

```
augugcgaac ccgccccacc uaagcccacu cagucugcuu ggcacaguuu ccccgaaugu    60
ccagcucucc ugcugcugcu cucccugcug uccugccccc ucgggcugcc ugugcugggc   120
gcuccuccaa gacucaucug cgacagcagg gugcuggagc gguacauccu ggaggcuaga   180
gaagccgaga augucaccau ggggugugcu cagggaugcu ccuucagcga gaacaucacc   240
gugcccgaca cuaaggugaa cuucuauaca uggaagcgga uggaugugg gacagcaggcc   300
cucgaagugu ggcagggccu cgcucugcug ucugaagcca uccugagggg acaggcccuc   360
cuggcuaaug ccagccagcc uucagagacc ccccagcugc acguggacaa agccguguca   420
agccugagau cccucacaag ccuccugagg gcucgggcg cucagaagga agccaugucu   480
cugccagagg aagccagccc ugccccacuc aggaccuuca cugucgauac ccugugcaag   540
cuguucagga ucuauuccaa cuuucugagg ggcaaacuga cacucuauac uggggaggcu   600
uguaggcggg gagaccgaug a                                             621
```

<210> SEQ ID NO 15
<211> LENGTH: 621
<212> TYPE: RNA
<213> ORGANISM: Artificial Sequence
<220> FEATURE:
<223> OTHER INFORMATION: A-rich sequence

<400> SEQUENCE: 15

```
augugcgaac cagcaccacc uaaaccaaca cagagcgcau ggcacagcuu cccagaaugc    60
ccagcacugc ugcugcugcu cagccugcua cugcugccac ugggacuccc aguccucgga   120
gcaccaccaa gacucaucug cgacagcaga gugcuggaaa gauacauccu agaagcaaga   180
gaagcagaaa acgucacgau gggaugcgca caaggaugca gcuucagcga aaacaucaca   240
gucccagaca ccaaagucaa cuucuacaca uggaaaagaa uggacguggg acagcaggca   300
cuggaagugu ggcaaggacu ggcacugcuc agcgaagcaa uccugagagg acaggcacug   360
cuagcaaacg caagccagcc aagcgaaacc ccacagcugc acguagacaa agcagugagc   420
agccuaagaa gccucaccag ccugcugaga gcacugggag cacagaaaga agccaugagc   480
```

```
cugccagaag aagccagccc agcaccacuc agaacauuca caguggacac ccugugcaaa    540
cuguucagaa uauacagcaa cuuccucaga ggaaaacuga cacuguacac gggagaagcu    600
ugcagaggag gagacagaug a                                              621
```